(12) United States Patent
Matousek et al.

(10) Patent No.: US 8,243,269 B2
(45) Date of Patent: *Aug. 14, 2012

(54) RAMAN SPECTRAL ANALYSIS OF SUB-SURFACE TISSUES AND FLUIDS

(75) Inventors: Pavel Matousek, Oxfordshire (GB); Anthony William Parker, Wiltshire (GB)

(73) Assignee: The Science and Technology Facilities Council, Oxfordshire (GB)

( * ) Notice: Subject to any disclaimer, the term of this patent is extended or adjusted under 35 U.S.C. 154(b) by 418 days.

This patent is subject to a terminal disclaimer.

(21) Appl. No.: 11/792,701

(22) PCT Filed: Nov. 25, 2005

(86) PCT No.: PCT/GB2005/004529
§ 371 (c)(1),
(2), (4) Date: Jun. 8, 2007

(87) PCT Pub. No.: WO2006/061565
PCT Pub. Date: Jun. 15, 2006

(65) Prior Publication Data
US 2008/0076985 A1    Mar. 27, 2008

Related U.S. Application Data

(60) Provisional application No. 60/669,880, filed on Apr. 11, 2005.

(30) Foreign Application Priority Data

Dec. 9, 2004 (GB) .................................... 0426993.2

(51) Int. Cl.
*G01J 3/44* (2006.01)
*A61B 6/00* (2006.01)
(52) U.S. Cl. ........................................ 356/301; 600/473
(58) Field of Classification Search .................. 600/310, 600/473–477; 250/358.1; 356/301, 318, 356/337, 342
See application file for complete search history.

(56) References Cited

U.S. PATENT DOCUMENTS

| 4,570,638 A | 2/1986 | Stoddart et al. |
| 5,139,025 A | 8/1992 | Lewis et al. |
| 5,194,913 A | 3/1993 | Myrick et al. |

(Continued)

FOREIGN PATENT DOCUMENTS

EP    1 475 037 A1    11/2004

(Continued)

OTHER PUBLICATIONS

2007 No. 770 Scientific Research—The Research Councils (Transfer of Property etc) Order 2007.

(Continued)

*Primary Examiner* — Michael Rozanski
(74) *Attorney, Agent, or Firm* — Birch, Stewart, Kolasch & Birch, LLP

(57) ABSTRACT

Apparatus and methods for determining, in-vivo, characteristics of sub-surface tissues or fluids in the human or animal body are disclosed. Incident radiation is supplied at one or more entry regions on a surface, and light is collected from one or more collection regions spaced from the entry regions. Raman features are detected in the collected light and depth related information derived therefrom.

66 Claims, 12 Drawing Sheets

U.S. PATENT DOCUMENTS

| | | | |
|---|---|---|---|
| 5,261,410 A | 11/1993 | Alfano et al. | |
| 5,349,961 A | 9/1994 | Stoddart et al. | |
| 5,371,368 A | 12/1994 | Alfano et al. | |
| 5,565,982 A | 10/1996 | Lee et al. | |
| 5,615,673 A | 4/1997 | Berger et al. | |
| 5,625,458 A | 4/1997 | Alfano et al. | |
| 5,660,181 A | 8/1997 | Ho et al. | |
| 5,752,519 A | 5/1998 | Benaron et al. | |
| 5,842,995 A * | 12/1998 | Mahadevan-Jansen et al. | 600/473 |
| 5,873,831 A | 2/1999 | Bernstein et al. | |
| 5,935,062 A | 8/1999 | Messerschmidt et al. | |
| 5,999,836 A | 12/1999 | Nelson et al. | |
| 6,289,230 B1 | 9/2001 | Chaiken et al. | |
| 6,310,686 B1 | 10/2001 | Jiang | |
| 6,321,111 B1 * | 11/2001 | Perelman et al. | 600/477 |
| 6,352,502 B1 | 3/2002 | Chaiken et al. | |
| 6,681,133 B2 | 1/2004 | Chaiken et al. | |
| 7,072,700 B2 | 7/2006 | Yamamoto et al. | |
| 7,652,763 B2 | 1/2010 | Matousek et al. | |
| 2003/0004419 A1 | 1/2003 | Treado et al. | |
| 2003/0018272 A1 | 1/2003 | Treado et al. | |
| 2003/0116436 A1 | 6/2003 | Amirkhanian et al. | |
| 2003/0220549 A1 | 11/2003 | Liu et al. | |
| 2004/0054270 A1 | 3/2004 | Pewzner et al. | |
| 2004/0133251 A1 | 7/2004 | Altshuler et al. | |
| 2004/0186383 A1 | 9/2004 | Rava et al. | |
| 2005/0010130 A1 | 1/2005 | Morris et al. | |
| 2010/0091276 A1 * | 4/2010 | Matousek et al. | 356/301 |

FOREIGN PATENT DOCUMENTS

| | | |
|---|---|---|
| GB | 2 311 854 A | 10/1997 |
| JP | 56022938 | 3/1981 |
| JP | 9-135825 A | 5/1997 |
| JP | 10-500323 A | 1/1998 |
| JP | H-11-508033 A | 7/1999 |
| JP | 2000-227421 A | 8/2000 |
| JP | 2001-178708 A | 7/2001 |
| JP | 2002-85385 A | 3/2002 |
| JP | 2002-512830 A | 5/2002 |
| JP | 2003-010189 | 1/2003 |
| JP | 2004-248849 | 9/2004 |
| JP | 2004-294150 A | 10/2004 |
| WO | WO 92/15008 | 9/1992 |
| WO | WO 95/26676 A1 | 10/1995 |
| WO | WO 96/26431 | 8/1996 |
| WO | WO 96/29925 A2 | 10/1996 |
| WO | WO-98/00057 A1 | 1/1998 |
| WO | WO 99/55222 A1 | 11/1999 |
| WO | WO 00/16036 | 3/2000 |
| WO | WO-00/20843 A1 | 4/2000 |
| WO | WO 01/39665 | 6/2001 |
| WO | WO 01/52739 | 7/2001 |
| WO | WO-02/07585 A2 | 1/2002 |
| WO | WO 03/023382 | 3/2003 |
| WO | WO 03/041123 | 5/2003 |
| WO | WO 03/068070 A1 | 8/2003 |
| WO | WO 03/073082 | 9/2003 |
| WO | WO-03/087793 A1 | 10/2003 |
| WO | WO 2004/051242 A1 | 6/2004 |
| WO | WO-2004/078044 A1 | 9/2004 |
| WO | WO-2004/078045 A1 | 9/2004 |
| WO | WO-2004/097365 A2 | 11/2004 |
| WO | WO-2005/004714 A1 | 1/2005 |
| WO | WO 2006/061565 | 6/2006 |
| WO | WO-2006/061566 A1 | 6/2006 |
| WO | WO-2007/040589 A1 | 4/2007 |

OTHER PUBLICATIONS

Dunsby C et al., Journal of Physics D. Appllied Physics, vol. 36, 2003, pp. R207-R227.

Matousek et al., Journal of Raman Spectroscopy, vol. 33, No. 4, 2002, pp. 238-242.

Matousek et al., Applied Spectroscopy, vol. 59, No. 4, 2005, pp. 393-400.

Dan Butterfield, "Through-package applications of Raman spectroscopy for nondestructive identification of product", Nov. 1999.

Haka et al., Cancer Research, vol. 62, Sep. 15, 2002, pp. 5375-5380.

Kathy Kincade, Optical diagnostics image tissues and tumors, Feb. 1996, pp. 1-5.

Takeshi Hasegawa, trends in analytical chemistry, vol. 20, No. 2, 2001, pp. 53-64.

Wu et al., Applied Optics, vol. 34, No. 18, Jun. 1995, pp. 3425-3430.

Ma et al., Applied Spectroscopy, vol. 51, No. 12, 1997, pp. 1845-1848.

Matousek., Journal of Raman Spectroscopy, vol. 32, 2001, pp. 983-988.

J. Klosowski and E. Steger, "Experiments on Raman Versus Primary Light Scattering Fluxes From Pressed Discs", Journal of Raman Spectroscopy, vol. 8, No. 3, 1979, pp. 169-171.

B. Schrader and G. Bergmann, "Intensity of the Raman Spectrum of Polycrystalline Substances", Fresenius Journal of Analytical Chemistry, vol. 225, 1967, pp. 230-247.

* cited by examiner

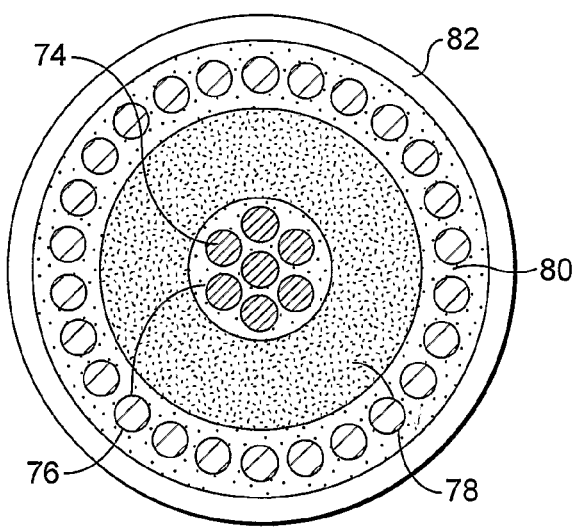
FIG. 7a
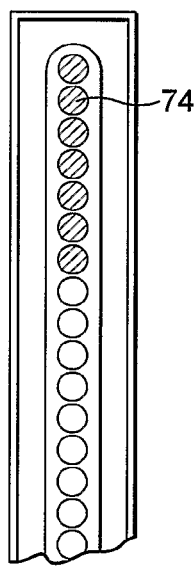
FIG. 7b
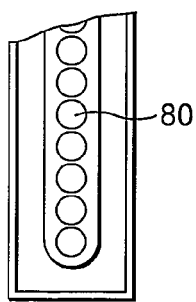

RAMAN SPECTRAL ANALYSIS OF SUB-SURFACE TISSUES AND FLUIDS

This National Phase application is a National Stage Entry of PCT/GB05/04529 filed on Nov. 25, 2005, and this application claims priority under 35 U.S.C. 119(e) to U.S. Provisional Application No. 60/669,880 filed on Apr. 11, 2005 and under 35 U.S.C. 119(a) to patent application Ser. No. 0426993.2 filed in Great Britain on Dec. 9, 2004. All of these prior applications are hereby expressly incorporated by reference into the present application.

FIELD OF THE INVENTION

The present invention relates to methods and apparatus for determining characteristics of in-vivo sub-surface tissues by detecting Raman features of diffusely scattered light. For example, the described methods and apparatus are suitable for detecting Raman spectral features of in-vivo bone through skin, nail and other surface tissues, without requiring exposure of the bone tissue by incision or puncture.

DISCUSSION OF THE PRIOR ART

The field of investigative studies of bone and other biological and living tissues encompasses a myriad of analytical techniques. Such techniques have been developed in response to the many situations in which it has been found to be important to assess the bone quality or tissue composition of a particular patient, human or animal. For instance, a person with osteoporosis has a significantly increased risk of bone fracture in comparison to the normal population. Diagnosis of degenerative skeletal diseases, for example osteoporosis, is important in allowing a sufferer to adapt their lifestyle or to seek intervention to mitigate the significant risk of fracture. A further example is found in musculoskeletal tissue research. An important aspect of this field is comparison of tissue composition and molecular structure with function using carefully selected populations of normal and, in many cases, transgenic animals.

To date however there are few non-invasive or minimally-invasive methods for examining details of bone or composition of other tissues. In studies of animal models of genetic or metabolic diseases, the standard procedure is to sacrifice animals and harvest tissue specimens for study. It would clearly be preferable to study living animals and with methods that cause minimal discomfort or harm. This need is most felt in studies that follow tissue changes over an extended period.

Sacrificial procedures are clearly not an option in examining human patients. The currently available methods of assessing bone quality are based primarily on radiography and, in particular, dual energy X-ray absorptiometry (DEXA). This technique however is only able to measure the inorganic phase of bone (hydroxyapatite) and the organic phase (primarily collagen I) is largely invisible. It is known that the material strength of bone is dependent on both the collagen and hydroxyapatite compositions. A crucial piece of data needed to assess bone quality is therefore neglected by the DEXA technique. To date, the only known procedures for obtaining organic (collagen) data involve analysis either of physically exposed bone or of a sample removed by biopsy. Both of these can often cause discomfort or pain to the patient.

Infrared and Raman spectroscopies provide a wealth of information on the physio-chemical state of a wide range of tissues and fluids (see, for example U.S. Pat. No. 6,681,133 or WO 01/52739). In bone analysis, for example, these techniques can provide information on mineral/matrix ratio, mineral crystallinity, matrix cross-linking and reversible and irreversible changes caused by mechanical loading. Unfortunately analysis by these methods has been limited to surface studies i.e. on exposed bone. Infrared radiation does not generally penetrate more than a few µm into tissue before being completely absorbed by water. The near-infrared range (700-850 nm) penetrates further, but multiple scattering causes loss of detailed spatial information. Confocal microscopy, a standard technique used to probe sample depths, is precluded on living tissue as a tight focal spot causes local heating and tissue damage. Moreover this technique is substantially less effective in diffusely scattering media, such as biological tissue, in which it is only practicable to depths of around ten times the mean free path of photons in the medium.

Elastically scattered photons have been used to probe beneath a scattering surface for compositional information. For example, B. B. Das, et al. in Rep. Prog. Phys. 60, 227 (1997) describes an approach using temporal gating. This technique relies on the fact that it takes a finite time for light to penetrate a diffusely scattering medium. Scattering events will therefore occur later at lower depths, and so monitoring a scattered signal over time should, theoretically, provide information as to the nature of the scattering centres at progressively greater depths.

The wide application of Raman spectroscopy to the extraction of information that can be critical to medical diagnosis has driven the search for a system that is capable of measuring sub-surface Raman scattering. Such a system should theoretically be capable of compositional analysis of bone and cartilage beneath the skin; of intravertebral disc tissue within a cartilage sack; of tendon and ligaments with differing material and functional properties; of gut wall or oesophageal tissue, which again are protected by a membranous coating in viva. The elastic scattering technique of Das et al. is however not directly extendable to Raman spectroscopy. Inelastic scattering of photons is a much weaker process due to far smaller cross-section for generating Raman light. This results in a much weaker signal. Furthermore the Raman signal is far more susceptible to interference from luminescence or sample damage.

One approach that has been used to obtain depth information from Raman scattering is described in "Three dimensional imaging of objects embedded in turbid media with fluorescence and Raman spectroscopy" by Jun Wu, et al., Appl. Optics 34(18), 3425 (1995). This paper describes a technique that exploits the fast rise-time of fluorescent decay and Raman scattering to infer depth information from the time delay between surface illumination and earliest detection of a scattered photon. A single-photon detection system is set to monitor back-scattered photons from a sample surface from the time it is illuminated by a 1 MHz pulsed laser beam. The spread in photon arrival times over a number of pulsed illuminations is shown to have an onset time delay that is characteristic of the depth of the scattering object.

The benefits that could be derived using non-invasive Raman probing of bones, where signal quality from bone can be crucial in arriving at an accurate and correct diagnosis as to whether disease is present, are apparent from A. Carden and M. D. Morris, J. Biomed. Optics 5, 259 (2000). However, conventional Raman signatures of bone collagen are masked by undesired Raman signals from overlaying tissue and so data on chemical composition is generally obtained by means of a biopsy.

There is a perceived need for an alternative non-invasive or minimally-invasive method of performing sub-surface Raman spectroscopy. Such a method should be capable of providing the basis for a more flexible in vivo analytical technique that overcomes the limitations of DEXA. In particular, DEXA is restricted to obtaining partial information relating to bone composition, whereas the more wide-ranging applicability of a Raman-based technique is desired.

SUMMARY OF THE INVENTION

It is an object of this invention, therefore, to provide an analysis technique based on Raman spectroscopy, that is capable of extracting sub-surface chemical compositional information of in-vivo and living tissues such as bone tissue. It is also an object of the invention to enable such analysis without requiring any incision, puncture or other surgical intervention to expose the target sub-surface tissue.

Accordingly, the invention provides a method of carrying out a sub-cutaneous inspection of sub-surface tissue or fluid, comprising: irradiating a surface tissue with a probe light beam; collecting light scattered beneath the surface, from one or more collection regions or locations on the surface, the collection regions being spaced from the probe beam; and detecting one or more Raman spectral features from the collected light. Biomedical or chemical characteristics may then be derived from the Raman spectral features.

More generally, the invention provides a method of determining one or more characteristics of a sub-surface tissue or fluid, through a diffusely scattering overlying tissue, comprising: supplying incident light at an entry region on a surface of the overlying tissue; collecting light scattered within the overlying tissue, from a collection region on the surface, the collection region being spaced from the entry region; and detecting, in the collected light, one or more Raman features, spectrally related to the incident light, which originate from the sub-surface tissue or fluid.

The overlying tissue may be skin or nail, and the sub-surface tissue or fluid may be bone, cartilage, breast tissue or blood, but there are many other applications, some of which may require surgical intervention to expose the overlying layer such as membranes or mucus covering and protecting an underlying layer, layers or organ to be studied. The tissue to be studied may be fluid in form, such as blood, lymph or fluid within a joint, an eye or between membranes.

Single entry and collection regions are sufficient in many cases to derive useable Raman spectral data. In other cases one or more entry and one or more collection regions of various physical spacings may be used, and the spectral data so obtained combined to yield a more accurate determination of the required characteristics of the sub-surface tissue, for example by using the data from multiple spacings to preferentially select the Raman signal of the sub-surface tissue.

A single or multiple collection regions surrounding or distributed about a central entry region are advantageous since this provides an increased collection area over a simple displaced collection region. Alternatively, a single or multiple entry regions surrounding or distributed about a single collection region may be used. Concentric annular or other shaped entry and collection regions may not be fully utilised. For example, a ring of closely packed terminating optical fibres may fill about 60% of the associated annulus. Preferably, at least 10% of the collection or entry annulus is optically utilised.

Preferably, associated entry and collection regions do not overlap.

The invention also provides associated methods of diagnosis of human or animal medical conditions, by interpretation of the determined characteristics of sub-surface tissue.

The invention provides corresponding apparatus for determining, one or more characteristics of a sub-surface tissue.

The present invention also provides a method of measuring, a sub-surface Raman spectrum of a diffusely-scattering tissue, the method comprising the steps of:
a) irradiating the tissue with a light probe;
b) collecting light scattered by the tissue; and
c) spectrally separating at least a portion of the collected light to detect one or more Raman spectral features,
wherein light scattered by the sample is collected from a plurality of spatial locations on the surface of the sample, each spatial location being at a different distance from the point of irradiation, at least a portion of the light collected at each spatial location being separately spectrally dispersed to form a plurality of Raman spectra and wherein the method further includes the step of:
d) analysing the plurality of Raman spectra to extract information on the Raman spectrum of a sub-surface region of the tissue.

Thus, with this method spectroscopic information is obtained non-destructively that can be interpreted to establish the nature and composition of a diffusely scattering tissue below a surface layer. The present invention effectively implements a form of spatial gating of the Raman signal obtained from the sample to isolate the Raman signal from a sub-surface layer which has a different composition to that of the surface layer. This method is referred to herein as Spatially Offset Raman Spectroscopy (SORS).

With the present invention for tissues having one or more different chemical compositions at differing depths within the sample, the collection of Raman spectra from regions spatially offset, by different amounts, from the point of incidence of the probe laser beam results in a series of spectra (two or more spectra) each spectra including Raman signals emanating from different depths within the tissue. The series of spectra taken contain different relative contributions of the Raman signals generated from the tissue surface layer and the tissue sub-surface layers. In collecting the data series, as the signal collection point is moved away from the point of incidence of the probe laser beam, the contribution of the surface layer signal diminishes much faster than for signals generated by different compositions at deeper layers within the bulk of the tissue. This enables the contribution of deeper, sub-surface tissues to be extracted either directly or by applying numerical processing to the collected spectral set for a higher degree of separation (e.g. multivariate data analysis or scaled subtraction of spectra from each other).

In a preferred embodiment two or more Raman spectra are collected and are analysed using a scaled subtraction, the Raman spectrum collected from or at a distance closest to the point of irradiation being subtracted from the Raman spectrum collected further from the point of irradiation, whereby features of the Raman spectrum for a sub-layer of the tissue are identified.

In a further alternative, where the Raman spectrum for the chemical composition of the surface of the tissue is known, the collected Raman spectra are analysed by scaled subtraction of the known Raman spectrum from the Raman spectra of the collected light.

In an alternative preferred embodiment at least twenty Raman spectra are collected at different distances from the point of irradiation and the plurality of Raman spectra are analysed using multivariate data analysis. Principal component analysis may be used as the multivariate data analysis.

A preferred feature of the present invention is irradiation of the tissue at two or more different wavelengths, where the collected light is a combination of a Raman spectrum and fluorescence, so that the Raman spectrum can be extracted from the collected light.

At least one of the tissue, the collection optics and the point of irradiation may be moved relative to the others to enable the collection of Raman spectra at different distances from the point of irradiation. For example, a movable stage could be provided on which a subject limb or head is mounted and the probe beam arranged to track the movement of the limb or head whereby the subject tissue is moved relative to fixed collection optics for the collection of scattered light at different distances from the point of irradiation.

The scattered light may be collected from point regions at different distances from the point of irradiation or the scattered light may be collected from a plurality of substantially parallel lines substantially transverse to the distance as measured from the point of irradiation.

Alternatively, the probe beam is supplied using optical fibres and the scattered light may be collected using optical fibres arranged in a plurality of concentric circles around the probe beam optical fibres whereby the scattered light is collected in concentric rings at differing radii from the point of irradiation.

Ideally, the light probe is at >200 nm and <2000 nm and may be generated by one or more quasi-monochromatic lasers or a diode laser which is tunable, for example with respect to temperature. To avoid haemoglobin absorption, the light probe is preferably >600 nm, and to avoid melanin absorption, a wavelength >800 nm is preferred.

In an alternative aspect the present invention provides apparatus for selective measurement of Raman spectra generated at different depths within a diffusely-scattering tissue, the apparatus comprising: a light source for irradiating a tissue with a probe beam; collection optics for collecting light scattered by the tissue and passing it to a spectrometer; detection means for detecting light dispersed by the spectrometer, wherein the apparatus is adapted for scattered light to be collected at a plurality of spatial locations on the surface of the tissue, each spatial location being at a different distance from the point of irradiation and at least a portion of the light collected at each spatial location being separately spectrally dispersed by the spectrometer to form a plurality of Raman spectra and wherein the apparatus further includes an analyser for identifying features specific to the Raman spectrum of a sub-layer of the tissue from the plurality of Raman spectra.

The light source may consist of one or more quasi-monochromatic lasers or a diode laser which are tunable, for example with respect to temperature.

In a further alternative aspect the present invention provides a method of diagnosis comprising collecting from a tissue, consisting of a surface region of an overlying tissue and a sub-layer region of a deep tissue which is different to the overlying tissue, one or more Raman spectra using the method as described above.

Preferably one or more features specific to the Raman spectrum of the sub-layer region of the tissue are identified in the one or more collected Raman spectra and are compared with those obtained from a healthy control specimen.

The methods and apparatus set out above may particularly be applied to determining characteristics of in-vivo tissues, in the human or animal body, and to determining biomedical characteristics of tissues.

The invention also provides apparatus as set out above incorporating an endoscope, to enable subcutaneous and internal tissues or fluids to be studied using the described Raman techniques.

Embodiments of the invention will now be described by way of example only and with reference to the accompanying drawings.

BRIEF DESCRIPTION OF THE DRAWINGS

FIGS. 7a and 7b show plan details of the optical head and connector of FIG. 6;

DETAILED DESCRIPTION OF PREFERRED EMBODIMENTS

Figure 1:
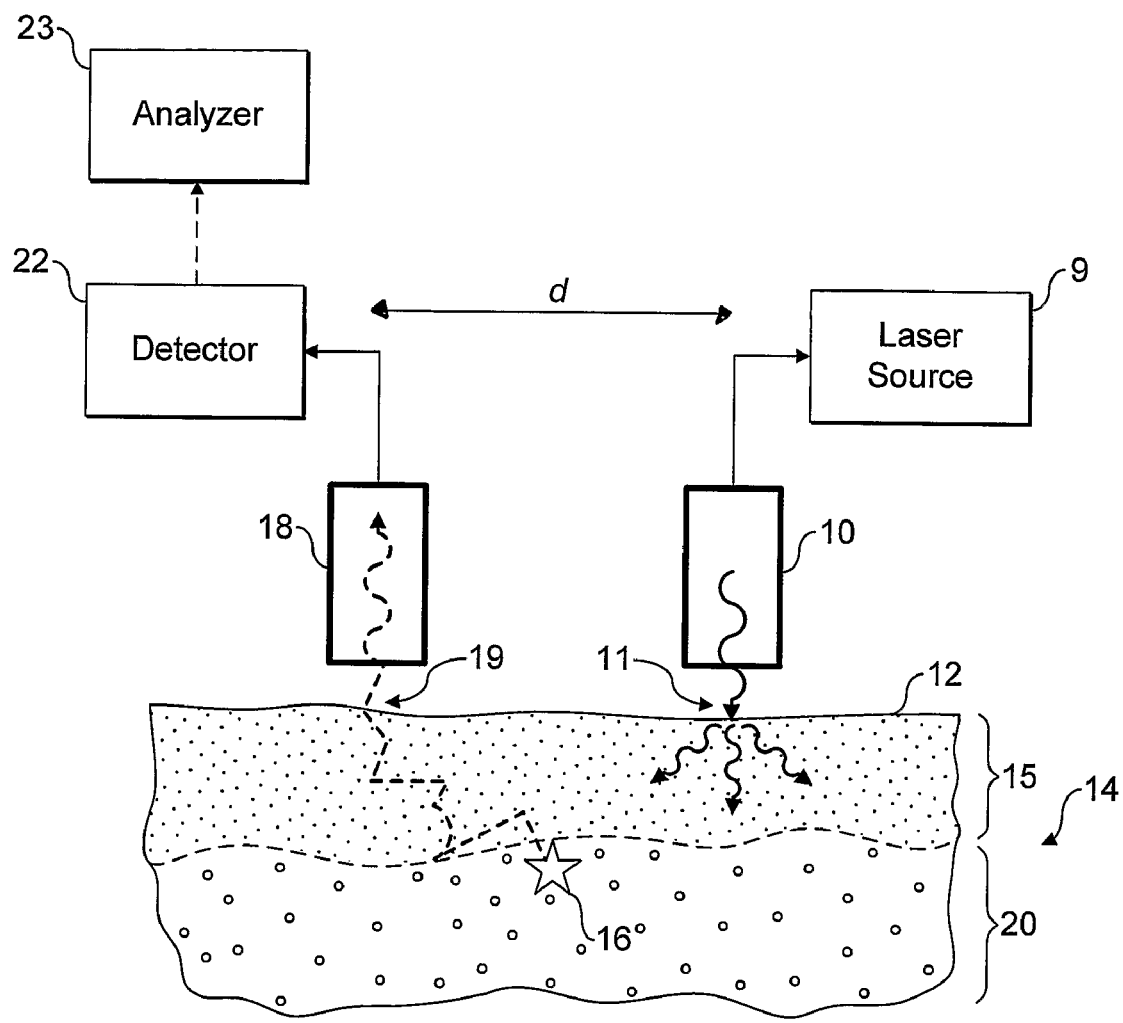
FIG. 1 illustrates principles of the invention, in which illumination by source 10 leads to Raman scattering 16 at in-vivo bone tissue.

Referring now to FIG. 1 an embodiment of the invention is shown in operation, in schematic cross section. A light source 10, incorporating or supplied by laser 9, is used to irradiate localised entry region of a surface 12 of in-vivo tissue 14, which in the present example is made up of a skin layer 15 and underlying bone tissue 20. The incident radiation from the light source is scattered diffusely through the sample, especially the upper skin layer. Some of the radiation may be absorbed by the tissue, some may give rise to optical emissions for example by fluorescence, and some re-emerges unchanged through the tissue surface 12.

A small proportion of the photons of the incident radiation are inelastically scattered giving rise to Raman photons, for example as illustrated by Raman event 16. The Raman photons in turn are diffusively scattered through the tissue. Some may be absorbed, for example giving rise to fluorescence, but some emerge unchanged through the surface 12 to be collected at collector 18.

The likelihood of a Raman photon undergoing a second Raman event is very small.

The collected light is analysed, for example using filters or a spectrometer, and a suitable sensor, in detector 22, and the determined Raman spectra or spectral features are used further in analyser 23. The detector may use a fourier transform rather than a dispersive spectrometry technique.

Typically, most Raman photons will be generated close to the light source 10, where the incident radiation is most intense. These Raman photons may best be detected by collecting light at the light source 10, for example by using optics common with the light source. As distance from the light source increases, however, the intensity of Raman photons originating near the light source falls away more quickly than the intensity of Raman photons originating further away from the light source, especially from deeper within the tissue. Preferential sampling of Raman photons from deeper within the tissue can therefore be achieved by spacing the location at which light in collected from the location at which the tissue is illuminated.

In FIG. 1 Raman event 16 occurs in or at the top of the sub-surface bone layer 20. The spacing d between the light source 10 and the collector 18, or equivalently between an entry region 11 and a collection region 19 can be adjusted to select for a particular depth. In preferred embodiments, however, light is collected at a range of spacings d, and analyser 23 is used to infer depth dependent characteristics of the tissue from the Raman features of the collected light for different values of d.

The Raman signal for a particular layer can be preferentially selected by numerical processing of the Raman signal at several spacings. Equally, the Raman signal for one or more layers can be preferentially rejected by similar numerical processing. Such numerical processing may be by simple weighted comparison or subtraction of signals from different spacings, or a more complex PCA technique could be used.

Figure 2A:
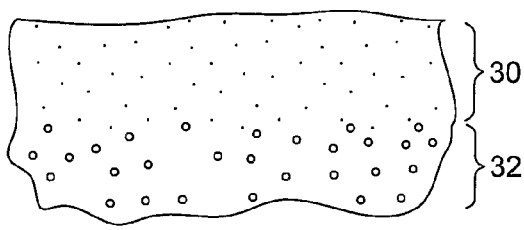
FIGS. 2a to 2c illustrate some different tissue configurations with which the invention can be used.
Figure 2B:
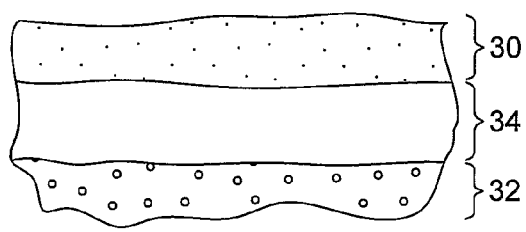
Figure 2C:
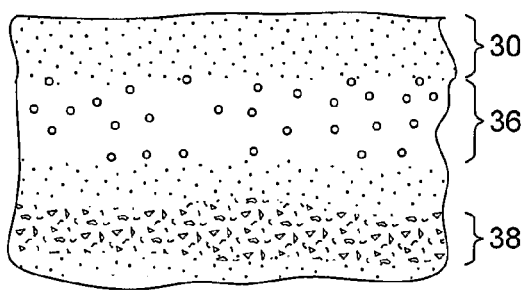

In FIG. 1 the in-vivo tissue 14 displays an abrupt boundary between the surface skin tissue 15 and bone tissue 20. In FIGS. 2a to 2c some other tissue configurations are shown. In FIG. 2a there is a gradual change from surface layer 30 to deep layer 32, and deep layer 32 may be diffusely scattering, or partly or completely opaque with Raman photons representative of layer 32 being generated in the interface between the layers. In FIG. 2b the surface layer 30 and the deep layer 32 are separated by a further transparent or semi transparent layer 34 which may be, for example, a space filled with a body fluid. In FIG. 2c a more complex tissue structure is shown, in which graduated or abrupt sublayers 36 and 38 are embedded beneath or within the surface layer 30.

The Raman techniques and apparatus used herein may be applied, for example, to non-invasive investigations for cancer tissue, either as a stand-alone technique to locate cancer affected tissue or in conjunction with existing techniques, such as mammography in the case of breast cancer. In a conjunction approach to breast cancer, mammography would be used to identify suspect regions within breast, and the Raman techniques would then be used to probe the suspect regions and identify their nature. This may alleviate the need for biopsy and provide immediate results, thus dramatically reducing patient trauma. The Raman techniques described are particularly suitable for deep-layer probing of breast, because breast tissue exhibits long photon scattering path lengths and low absorption coefficients compared to many other types of tissue.

Where appropriate, the Raman apparatus may be combined into an endoscope arrangement. In this manner, body cavities may be probed, or partially invasive techniques used to probe body areas that should preferably not be disrupted, but where Raman probing through surrounding tissue or membrane into the areas is desired. Example areas are brain (for example to identify Alzheimer's and Hutchinson's diseases and CJD), liver, heart, kidney, prostate gland, veins, nervous system, spinal cord and kneecap. Other target physiological conditions include probing for the nature of stones in kidney and bladder.

The described Raman methods and apparatus may also be used for the non-invasive detection of blood characteristics, especially through skin. In this application, the invention is used to reject the overwhelming Raman and fluorescence signal originating from the skin to reveal the underlying signal from blood contained in blood vessels. In this way, glucose levels, oxygenation, micro organisms, types and amounts of cholesterol, and other blood components such as urea, total protein and albumin may be detected and measured. Other fluids such as lymph and eye fluids may be studied.

To improve coupling between the tissue and the light source and/or collector and index matching fluid may be used. An index matching fluid, such as glycerol, may also be deposited into tissue to locally and temporarily reduce photon scattering. This increases the workable depth of the described techniques. The index matching fluid may be referred to as a "contrasting agent" or "image enhancing agent".

Figure 3A:
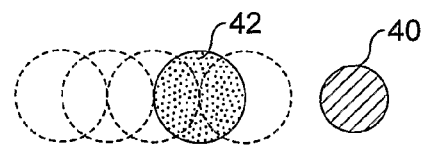
FIGS. 3a to 3c illustrate various entry and collection region arrangements.

The incident irradiation and collection of light at a single, at multiple or at a variable spacing can be achieved using a variety of geometries. In FIG. 3a there is a single illumination or entry region 40 on the sample surface. Spaced from this illumination region is either a single collection point or region 42, or multiple regions as indicated by the broken lines. Alternatively the single collection region, or equivalently the illumination region may be moved to provide a variable spacing.

Figure 3B:
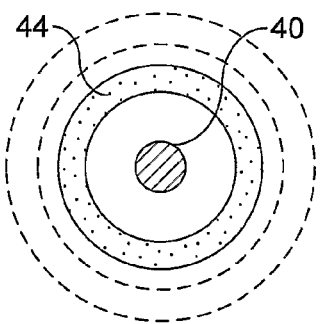

In FIG. 3b the single illumination region 40 is surrounded by an annular collection region 44, or by multiple or a variable radius annular collection region as indicated by the broken lines. Instead of an annular collection region, a broken annulus or multiple separate regions at similar distances from the point of illumination could be used.

Figure 3C:
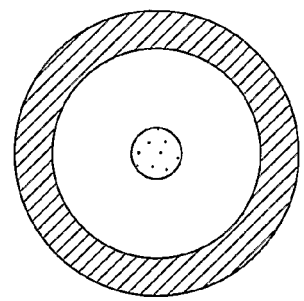

In FIG. 3c an annular illumination region 46 and central collection point 48 are used, thereby reducing the localised intensity of incident radiation required to generate a given number of Raman photons. The annulus may be varied in radius or be provided as multiple annuli having a range of radii. A broken annulus of multiple separate illumination regions distributed at similar distances from the central point of collection could also be used.

Generally, it is beneficial to collect light, or to provide incident radiation at as large a proportion of an entry or collection region as possible. However, in practical embodiments the coverage may be limited. For example, in arranging cylindrical optical fibres in an annulus a coverage of 10% may be adequate, but 25% would be preferred and 60% or more may be possible.

In simplistic embodiments a single entry region may be provided by a single optical fibre brought close to the sample surface, and multiple collection regions may be provided by a linear array of collection fibres. Optical fibres may be similarly used to provide annular and other configurations of single and multiple fixed spacings and various mechanical arrangements may be used to provide variable spacings.

Figure 4:
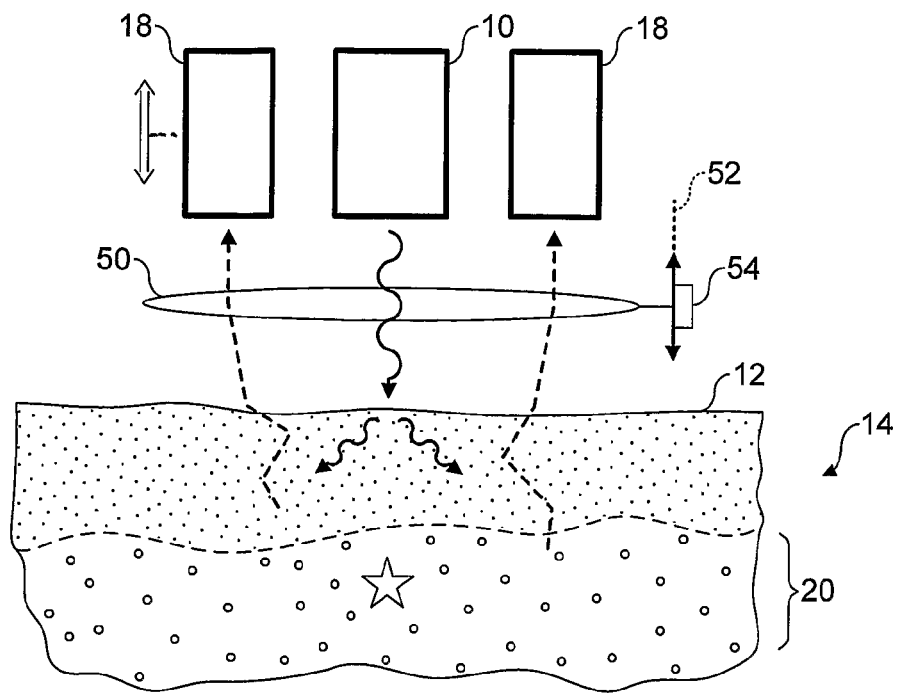
FIG. 4 illustrates an arrangement for varying the diameter of an annular collection region using an optical arrangement 50, 54.

To provide a variable radius entry region or collection region an optical arrangement such as that illustrated in FIG. 4 may also be used. Optics 50 located between the tissue and the collector, and/or sample-to-detector distance, is adjustable to direct light from different parts of the tissue surface onto collector 18 which is concentric with the light source 10. A lens arrangement (and/or the illumination source and Raman collector/detector) which can be translated in an axial direction 52 by an optics drive 54 directs light from an annular region of varying radius onto the collector, but other configurations are also envisaged.

Figure 5:
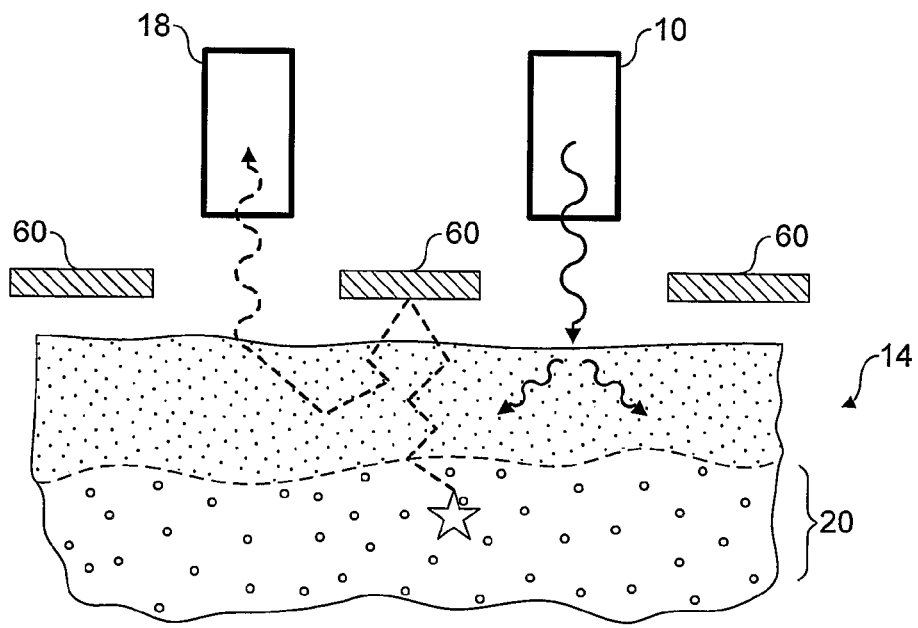
FIG. 5 illustrates the use of mirrors 60 to enhance the collection of Raman photons.

A further aspect, which may be used with any of the arrangements discussed above, is illustrated in FIG. 5. One or more mirror elements 60 are presented to the sample surface. When either incident or Raman radiation emerges from the tissue away from the collector 18, these mirror elements redirect the emerging radiation back into the tissue. This increases the intensity of incident radiation and so the generation of Raman photons within the tissue, and also increases the proportion of Raman photons received at the collector 18. The mirror elements are preferably absent from the surface adjacent to the light source 10 or entry region, and adjacent to the collection regions.

In alternative embodiments non-imaging optics, such as those described in Applied Optics vol 35 p 758, may be used to achieve higher collection efficiency by use of a mask placed directly onto the tissue surface, or placed in an image plane if other imaging optics are also used. The mask blocks appropriate areas of the tissue to collect signal from a desired spatial offset only. The masking is preferably synchronised with a detector such as a charge coupled device such that sequential readings from the detector relate to masks providing light collected from correspondingly sequential spacings between the illumination and collection regions. The masking could be mechanical and could also be performed between imaging optics and a non-imaging type detector.

Figure 6A:
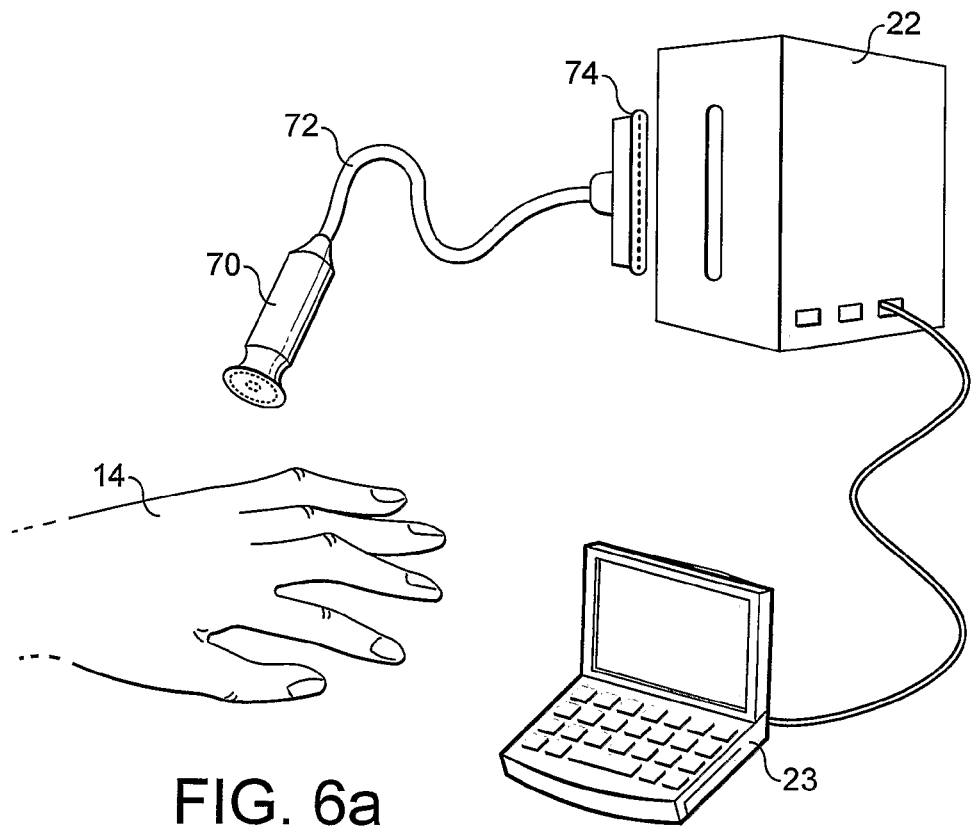
FIG. 6a shows an optical head for sub-surface in-vivo tissue analysis, for coupling to spectral detector 22.

FIG. 6a illustrates a practical embodiment of the invention comprising an optical head 70 coupled by an optical fibre bundle 72 to detector 22. The results of the optical detection are fed to a laptop or other computer 23 which analyses the Raman features to infer characteristics of the tissue 14. Detail of the optical head 70 is shown in the plan schematic view of FIG. 7a (which is not to scale). A bundle of light source optical fibres 74 terminate in the central region of the head. These light source fibres are embedded in a filler 76 such as epoxy, and surrounded by an annular spacer element 78. Collection optical fibres 80 terminate in an annular region surrounding the spacer element, again embedded in a filler, and surrounded by an external casing. This arrangement may be adapted to included the various mirror and optical arrangements discussed above.

In this particular embodiment each optical fibre has a core of 200 μm diameter and a cladding bringing the fibre thickness to 230 μm. The inner bundle consists of seven light source optical fibres 74, and the outer bundle consists of 26 collection optical fibres 80. The spacer 78 is sized to space the collection fibres 80 about 3 mm from the centre of the head, and the terminations of the collection fibres are distributed approximately evenly in an annulus of constant radius about this centre. The collection fibres should be suitable for carrying out optical or near infra red Raman work, and may be made of silica.

The illumination and collection optical fibres terminate, about 100 cm distant from the optical head, in a connector illustrated schematically in FIG. 7b. The connector presents the six illumination and twenty six collection fibres for coupling into the detector 22 of FIG. 6, which incorporates a light source illumination quasi-monochromatic laser operating at 827 nm and a Kaiser Holospec optical analyser.

Figure 6B:
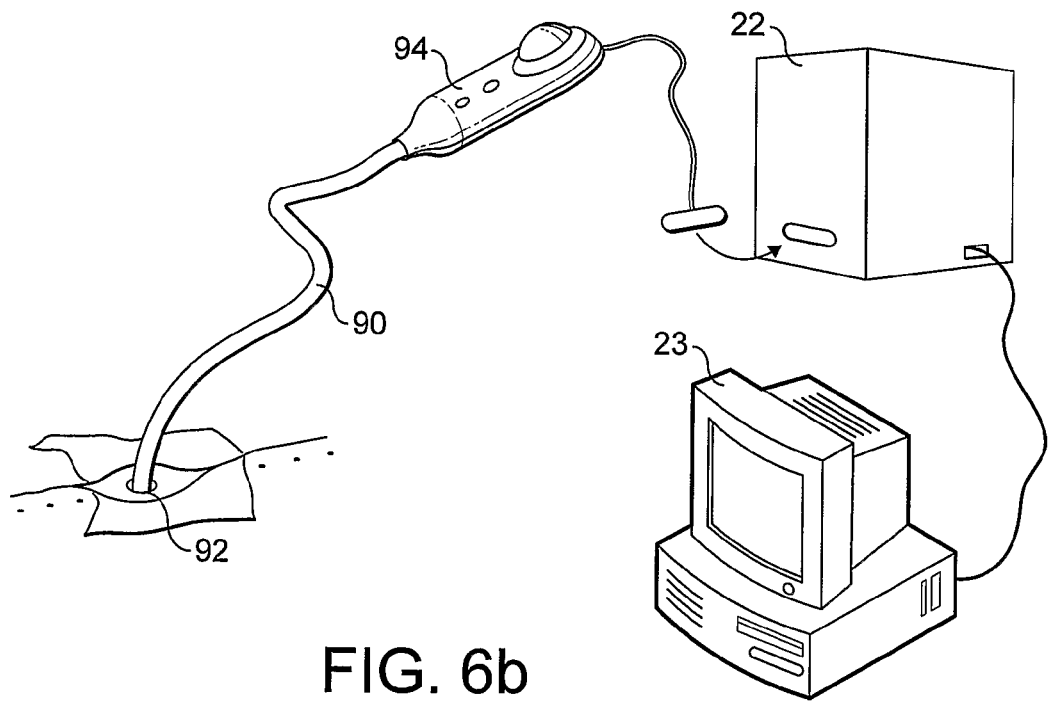
FIG. 6b shows an endoscope incorporating the invention.

In FIG. 6b the invention is implemented as an endoscope. An insertion tube 90 is used to enter a human or animal through a natural or surgically formed orifice 92. The illumination and collection fibres terminate in a detection head (not shown) and pass back through the insertion tube to a control handle 94. Optical detection may be carried out in the control handle or in a connected detector unit 22.

Figure 8:
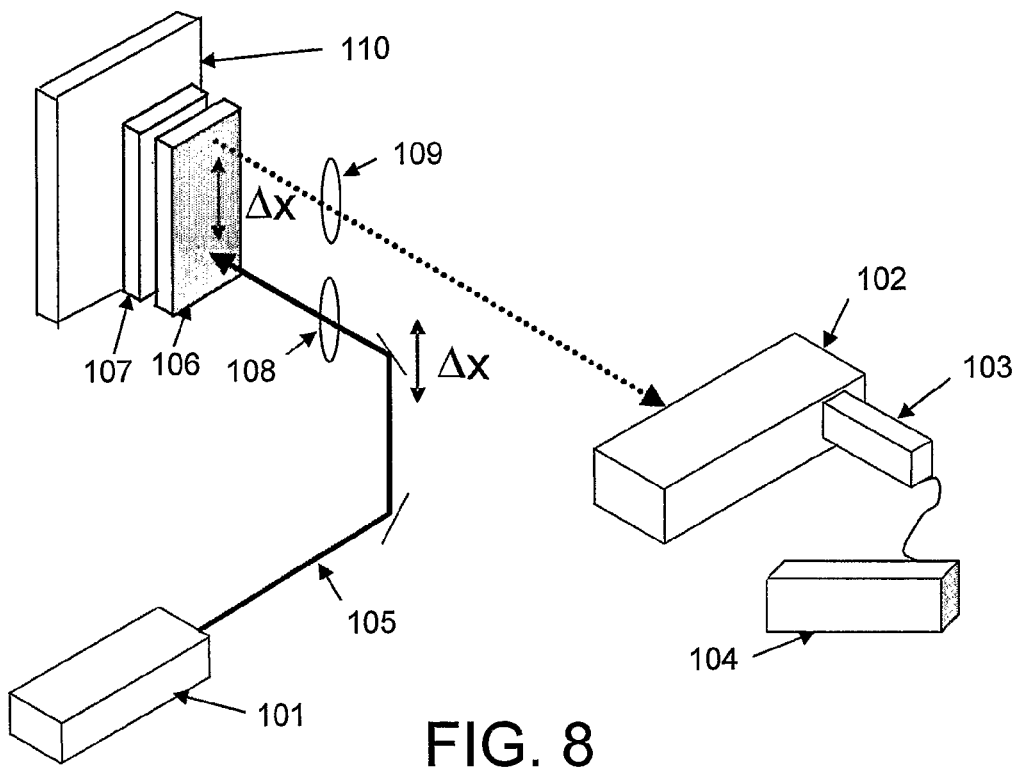
FIG. 8 illustrates schematically analysis apparatus in accordance with the present invention set up to extract Raman spectra generated beneath a surface layer of a sample representative of in-vivo tissue.

A schematic diagram of another spatial gating analysis apparatus for identifying depth specific Raman spectra from in-vivo sub-surface tissues is shown in FIG. 8. Features and variations described below may be applied to the more general embodiments already discussed, as appropriate. The apparatus generally comprises a laser 101, Raman detection apparatus 102, 103 and an analyser 104. The probe beam 105 of the apparatus is generated using a quasi-monochromatic laser such as a diode laser, preferably operating at 827 nm in the case of tissue analysis, with 12 mW power which is directed using conventional optics at a sample. The sample has a surface layer 106 and a deeper layer 107 of a different chemical composition to that of the surface layer.

The actual set up illustrated in FIG. 8 is experimental. The layers of the sample constitute a mock-up of actual in-vivo tissue, and for convenience are mounted on a stage. However, it is straightforward to substitute real in-vivo tissue with little modification. In the present demonstration an argon ion laser operating at 514 nm was used.

With this apparatus the laser plasma lines were blocked using a Pellin-Broca prism (not illustrated). The apparatus includes a 1 m focal length lens 108 for weakly focusing the laser beam onto the sample to a spot diameter of 300 μm and at normal incidence. Raman light produced as a result of the irradiation of the sample is collected in backscattering geometry using a 2" diameter collection lens 109 with f-number ~1 and is imaged with the lens 109 onto the slit of a spectrometer 2, which is part of the Raman detection apparatus, with a magnification of 2.5. A conventional imaging spectrometer 102 (for example a Spex Triplemate™ with f-number 6.3) is preferably used to disperse the Raman light and image the Raman light onto a CCD camera 103. The camera 103 is preferably a liquid nitrogen cooled back-illuminated deep depletion CCD camera (for example Andor, DU420-BU2 (250 nm) 1024×255 active pixels). The CCD quantum efficiency of such a camera in the region of Raman spectra is around 65% and has a pixel size of 26×26 μm. The final stage slit width of the spectrometer 102 was set to 120 μm. The CCD was binned vertically across 20 pixels to maintain the spatial selectivity on the collection side.

Figure 9:
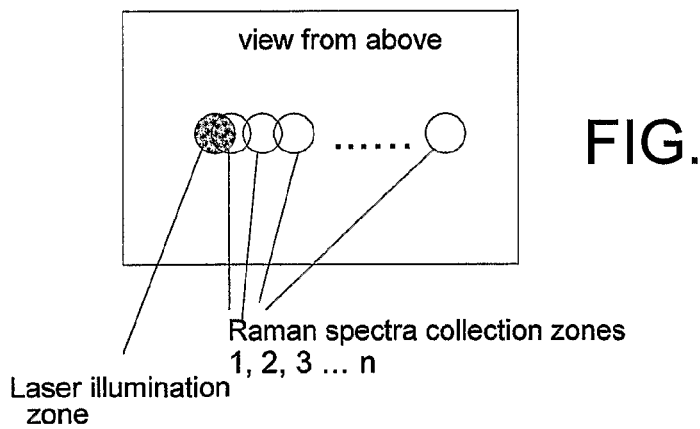
FIG. 9 illustrates a point collection geometry for collection of spatially offset Raman spectra in accordance with the present invention.

The sample 106, 107 was mounted on an x-y-z micropositioning stage 110 which includes a controlled drive (not illustrated) which moves the stage (vertically in FIG. 8) together with the final optics to keep the incidence point of the laser beam fixed on the sample with respect to the sample. In this configuration, the Raman detection apparatus 102, 103 always collects back scattered Raman shifted photons from a fixed imaging zone in space and the sample is scanned across this imaging zone whilst the pump beam incidence point remains fixed in its position on the surface of the sample. A filter (not illustrated) may also be used to block any residual elastically scattered probe laser light from reaching the spectrometer 102. The SORS apparatus described above may be deployed using a point collection laterally offset from the point of probe beam incidence (FIG. 9). Alternatively, a movable stage or other movement control means may be used for achieving relative movement between one or more of the sample, point of irradiation and the Raman detection apparatus.

Raman spectra using apparatus similar to that described above were collected for a test sample similar in optical behaviour to a layered diffusive in-vivo tissue, in which the first layer 106 consisted of a 1 mm optical path cuvette of 1 cm width and ~4 cm height, with 300 μm custom made fused silica front and back windows, filled with PMMA (poly(methyl methacrylate)) spheres of ~20 μm diameter. The spheres were loosely packed in the cell using mechanical tapping on the cell during filling to eliminate any larger voids. This first layer was followed by a second layer 107 consisting of another cell of 2 mm optical path filled with trans-stilbene fine powder ground using a mortar and pestle. The cuvettes 20 were employed in order to provide a simple method of sample handling and are not an essential feature of the apparatus.

Figure 10:
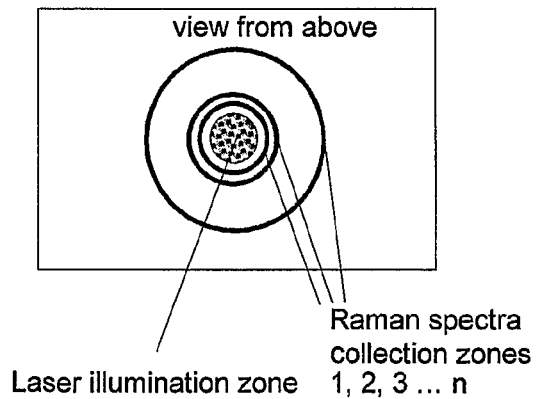
FIG. 10 illustrates a concentric circle collection geometry for collection of spatially offset Raman spectra in accordance with the present invention.

With the probe laser beam incident on the sample positioned with the first layer 106 uppermost, spatially offset Raman spectra using the SORS method described herein were collected using a basic point collection geometry in which collection is from points laterally displaced from the probe beam's incidence point (FIG. 9). The point of collection geometry as illustrated in FIG. 9 represents the simplest implementation of the method of the present invention. On the other hand, the concentric circle geometry illustrated in FIG. 10, which does not require the use of an x-y positioning stage, advantageously yields much higher collection efficiency but involves the use of optical fibres to image the individual circles at different heights on the spectrometer slit enabling their imaging after dispersion on the CCD 103 onto separate horizontal strips with the vertical position of the spectra on the CCD corresponding to a given offset collection distance on the sample surface with respect to the probe beam's incidence point. The use of a fiber optic bundle for the collection of Raman spectra is described in an article by Jiaying Ma and Dor Ben-Amotz entitled "Rapid Micro-Raman Imaging using Fiber-Bundle Image Compression" Applied Spectroscopy Vol. 51, No. 12, 1997 the contents of which is incorporated herein by reference.

It will, of course, be apparent that further alternative collection geometries could be employed whilst still achieving spatially offset Raman spectra collection in accordance with the present invention.

Additionally, with no sample illumination, an "above the sample" Raman spectrum may be collected which represents background and apparatus noise. This "above the sample" Raman spectrum can then be subtracted from the set of Raman spectra to remove noise from the spectra.

When taking Raman spectra using the resonance Raman technique, whereby the wavelength of the incident probe beam is tuned to match chromophores of the material or materials being investigated, the Raman signatures may be swamped by fluorescence (luminescence) generated from electronic excitation. For example, fluorescence will be stimulated in room temperature or in-vivo studies of bone, but phosphorescence is more likely in colder samples. Similarly, Raman probing of metallic systems will often stimulate room temperature phosphorescence.

In such cases the Raman spectra can be recovered using the SORS method at two or more laser wavelengths. This relies upon the fact that the spectral profile of a fluorescent background is not normally dependent on the excitation wavelength whereas the Raman spectrum is dependent on the excitation wavelength. Hence, spectra collected at the same spatial distance from the point of illumination at two or more different wavelengths of irradiation may be subtracted from each other to give a derivative type plot of where the Raman bands are and this can be mathematically processed to give a truer looking Raman spectrum. This technique for identifying Raman bands is described in an article by S. E. J. Bell, E. S. O. Bourguignon and A. C. Dennis entitled "Subtracted shifted Raman spectroscopy (SSRS) method" Analyst, 1998, 123, 1729-1734. This technique is also referred to as the Shifted Excitation Raman Difference technique (SERD) as described in a paper of the same name by P. Matousek, M. Towrie and A. W. Parker I J. Raman Spec., 33, 128-242 (2002) the contents of which is incorporated herein by reference.

The two or more wavelengths of incident irradiation may be generated by means of separate lasers or by means of a single laser, such as a diode laser, the output of which is varied for example through temperature tuning. The difference in wavelength required is generally about half the width of the Raman bands, typically approximately 5-10 $cm^{-1}$.

Figure 11:
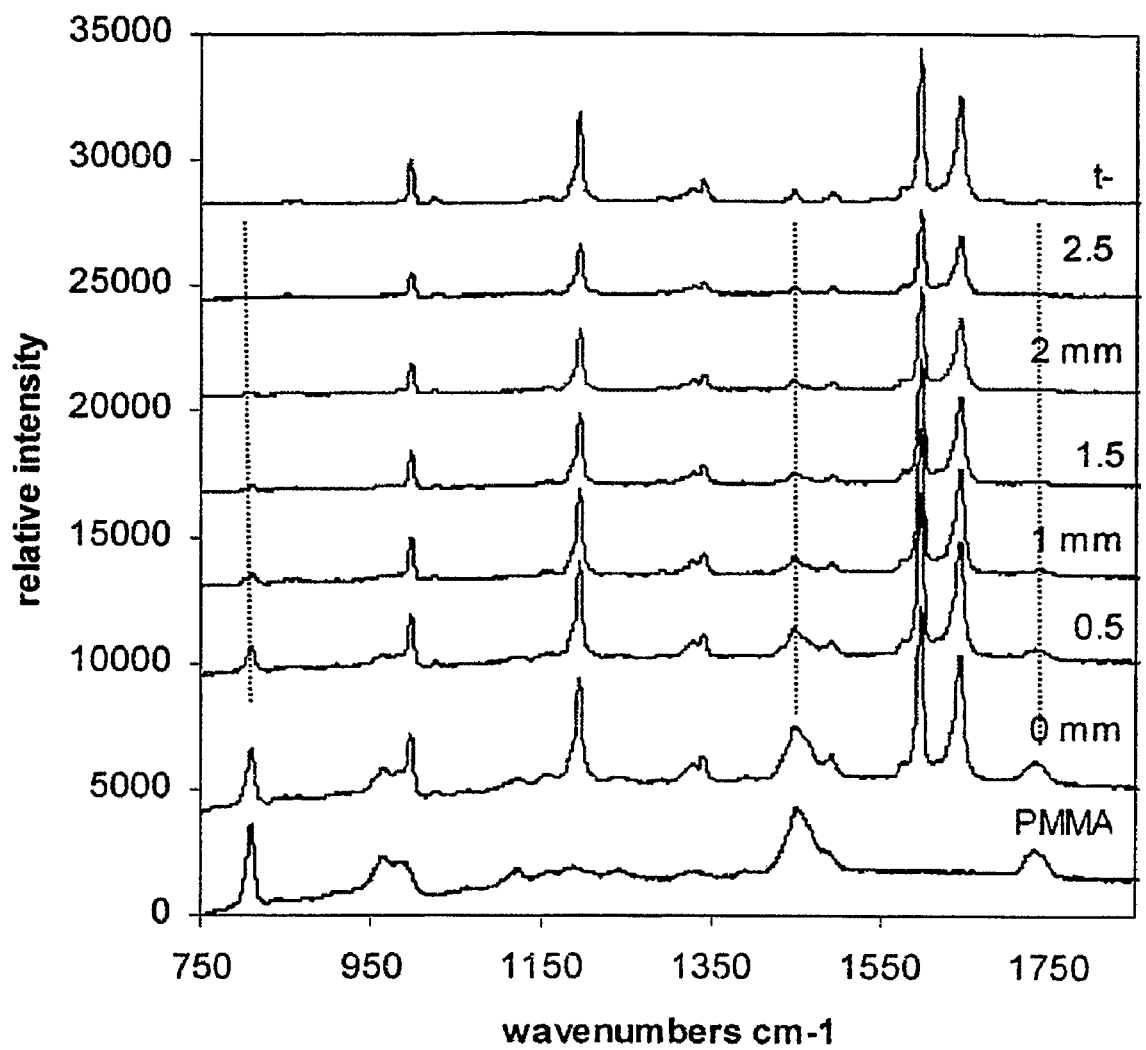
FIG. 11 shows a series of Raman spectra for a two layer sample generated at different offsets using the analysis apparatus of the present invention.

A set of Raman spectra for the test sample described above, measured with a varying degree of spatial offset with respect to the Raman collection point and the point of laser incidence on sample surface is shown in FIG. 11. For comparison, the Raman spectra of pure layers measured in separate measurements are also displayed. The top spectrum in FIG. 11 is that of pure trans-stilbene and the bottom spectra that of pure PMMA. The spectrum measured with the zero offset (0 mm) represents the Raman spectrum one would typically obtain using a conventional Raman instrument. It is evident that it contains an appreciable contribution from both the top and bottom layers of the sample and that the contribution of the top layer gradually decreases with offset distance in the spatially offset spectra. For real applications, where a pure spectrum of the bottom layer needs to be recovered, the top layer signal might represent an unacceptable distortion to the Raman signal of a lower layer. The gradual separation between the two signals is clearly accomplished using the SORS approach as the lateral offset between the Raman collection point and the point of probe beam incidence is increased and is clearly observable from the illustrated data set. At a distance of >2 mm (third spectra down in FIG. 11) an order of magnitude improvement in the ratio of the lower over the top layers Raman signals is achieved.

Figure 12:
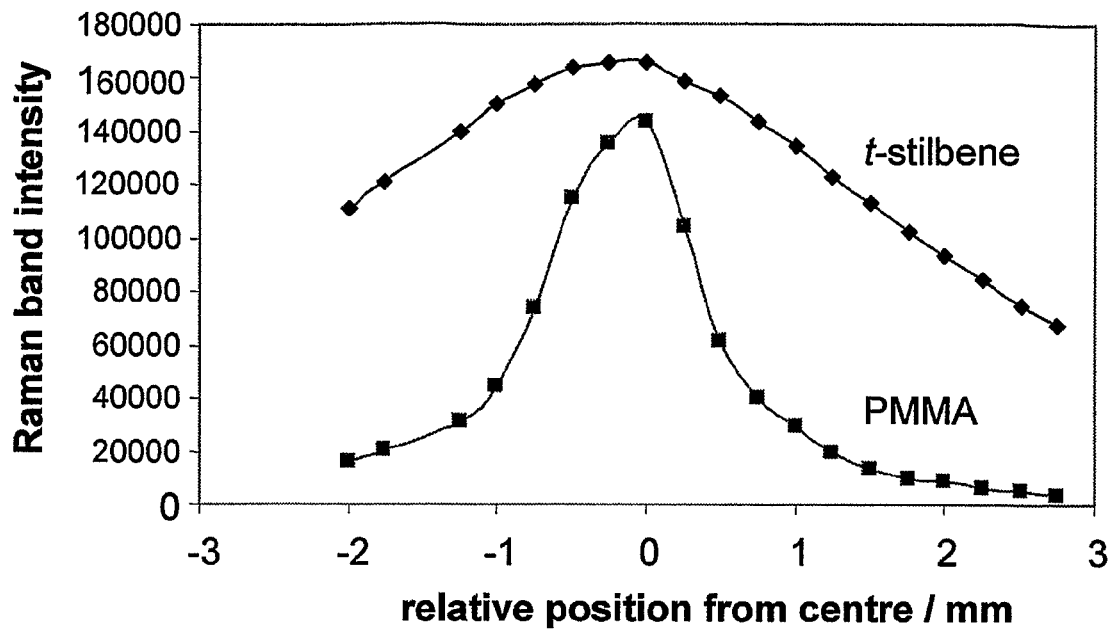
FIG. 12 illustrates the dependence on offset distance of the absolute intensities of the Raman spectra for the sample of FIG. 11.
Figure 13:
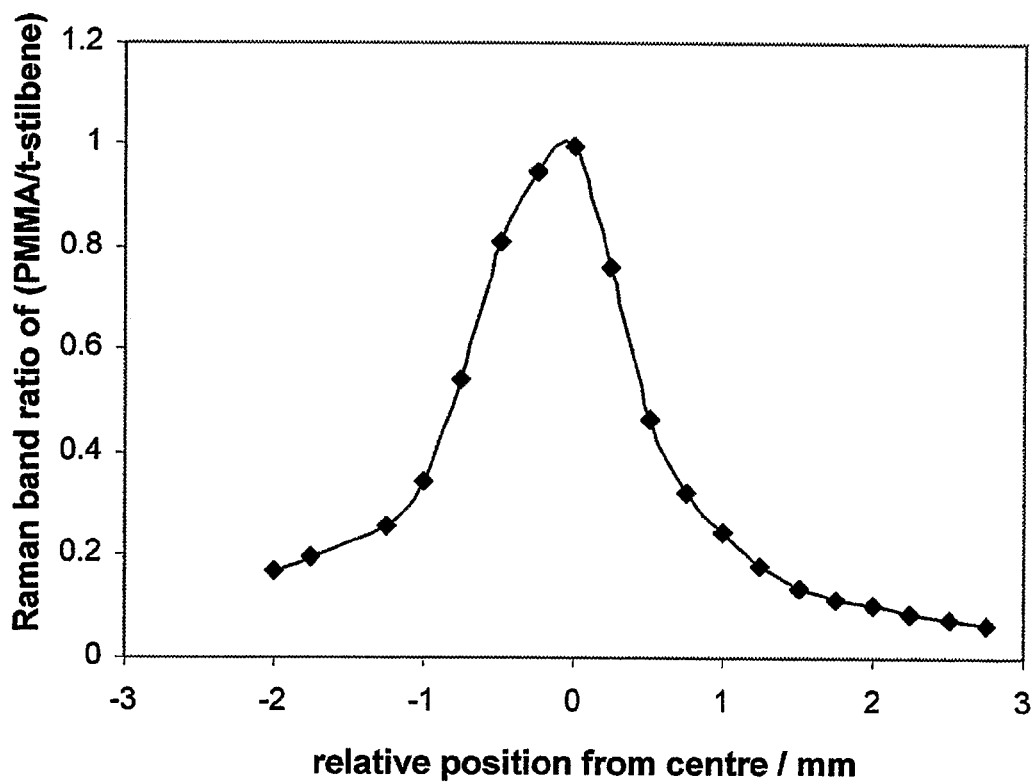
FIG. 13 illustrates the ratio of the Raman spectra of FIG. 12 with respect to offset distance.

FIG. 12 shows the dependence of the absolute Raman intensities of the individual spectra on the spatial offset. The data was obtained by numerical fitting of two intense trans-stilbene bands at 1575, 1595, 1632 and 1641 $cm^{-1}$ and bands at around 809, 1455, and 1728 $cm^{-1}$ for PMMA. The plot clearly demonstrate that as the Raman collection point is moved sideways from the probe illumination zone, i.e. the lateral offset is increased, the Raman signal from the bottom layer diminishes much more slowly than that from the top layer. This results in the overall relative Raman intensity ratio of the bottom over the top layer improving with increasing spatial offset as shown in FIG. 13.

Figure 14:
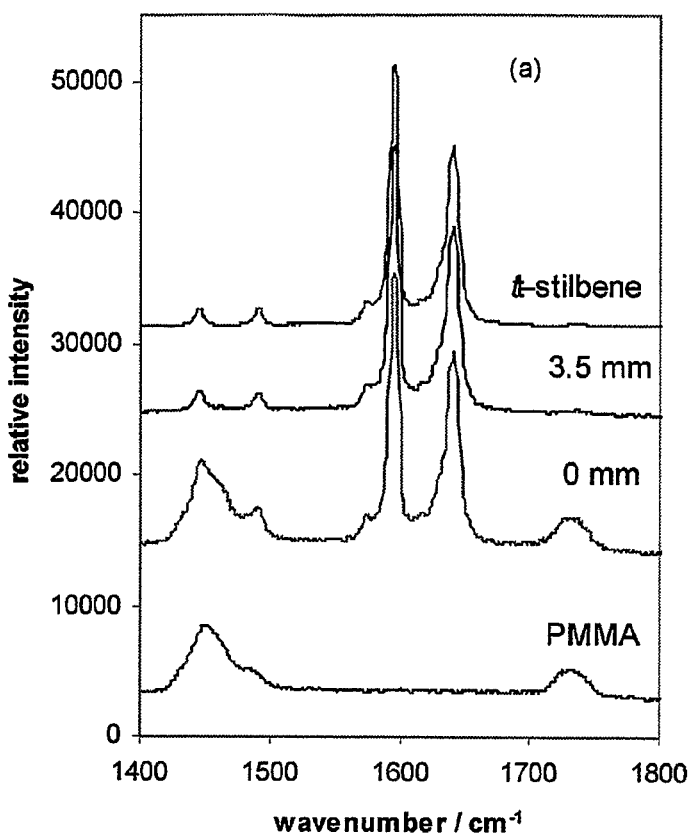
FIG. 14 shows a series of Raman spectra for the same two layer sample scaled to the same height of trans-stilbene bands.
Figure 15:
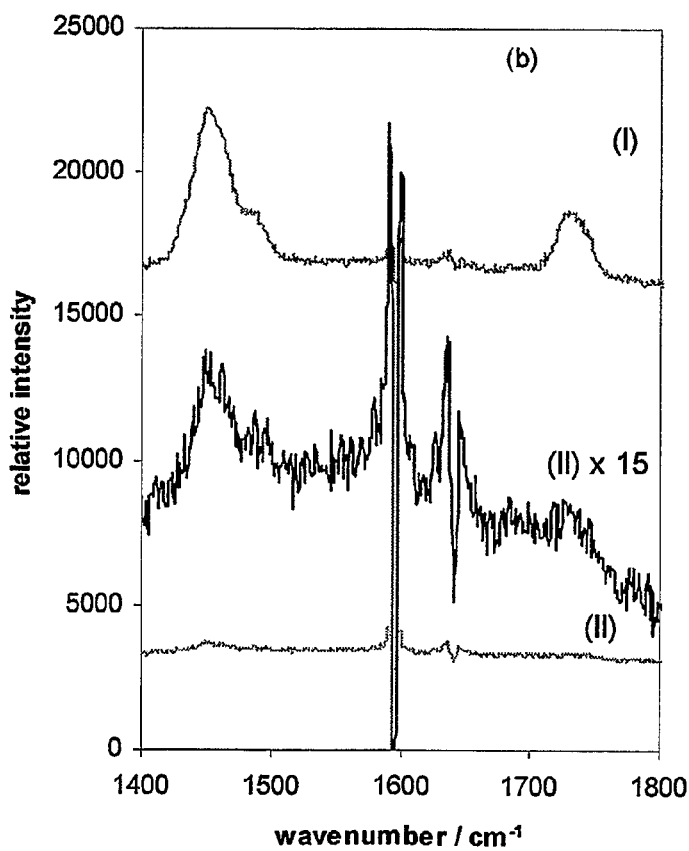
FIG. 15 illustrates the PMMA contributions within the individual spectra of FIG. 14.

To quantify the contrast improvement achieved using the method and apparatus of the present invention with respect to the test sample described above, a Raman spectrum with a longer acquisition time (1000 s) at an offset of 3.5 mm was acquired. FIG. 14 shows this spectrum along with a Raman spectrum acquired with zero offset scaled to the same height of trans-stilbene bands. By subtracting the pure trans-stilbene spectrum from these spectra we obtained the PMMA contributions within the individual spectra (see FIG. 15). By fitting these we established that the contrast of the lower layer had been improved by a factor of 15 by rejecting the top layer spectral component. Another striking observation is that the signal-to-noise obtained using this spatial gating approach is good in comparison to alternative approaches.

The total attenuation of the Raman trans-stilbene signal by the 1 mm PMMA layer was measured with the zero offset to be around 80. This loss of signal through the diffusion process, inevitably present also in conventional Raman spectroscopy, can be, however, effectively offset through further refinements in the collection efficiency: for example by adopting the circular collection geometry shown in FIG. 10 or by using a lower f-number and a higher throughput spectrograph.

Figure 16:
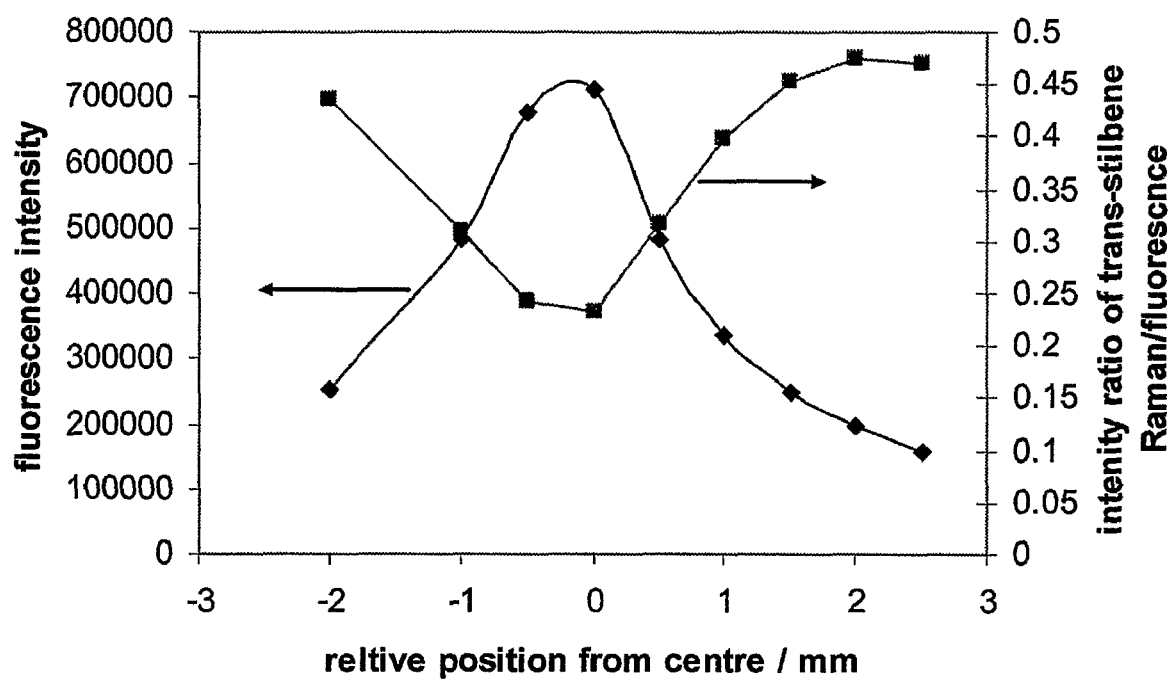
FIG. 16 shows, for the same sample, the relative ratio of a trans-stilbene Raman signal in comparison with fluorescence originating from the PMMA layer as a function of the spatial collection offset.

FIG. 16 demonstrates another useful feature of the spatial gating analysis apparatus and method of the present invention. The analysis apparatus is capable of suppressing fluorescence in the lower layer Raman spectrum if it originates from the top layer. The plot shown in FIG. 16 gives the relative ratio of the trans-stilbene Raman signal in comparison with the fluorescence originating from the PMMA layer as well as the fluorescence absolute intensity as a function of the spatial collection offset. The trans-stilbene Raman intensity relative to fluorescence intensity is improved by a factor of approx. 2 with the introduction of a 2.5 mm displacement.

In a situation where a larger separation of the data obtained from surface and sub-surface layers is required than that achievable directly within the raw spectra, by offsetting the collection and probe launch points a multivariate data analysis procedure may be deployed using the analyser 104 of FIG. 8. The data collected by SORS is particularly amenable to multivariate data analysis because for this approach to be applicable, the set of Raman spectra measured at various offsets is still required. To achieve an effective numerical decomposition the number of spectra within the set should ideally be at least an order of magnitude higher than the number of layers present in the sample. To demonstrate this a multivariate analysis of the form of principal component analysis (PCA) was employed.

Approximately twenty Raman spectra acquired on the PMMA and trans-stilbene two-layer system represented in FIG. 8 and produced using the SORS method and apparatus described herein were imported into Matlab™ R11 (The Mathworks Inc., Natick, Mass.) and processed with both built in and locally written scripts. The ten largest eigenvectors generated after performing a singular value decomposition on the original data set were included in the PCA rotation. The pure spectra of PMMA and trans-stilbene were not included in this dataset and no baseline correction was performed.

Multivariate data reduction techniques are advantageous when a complete separation of the spectral features of the surface and sub-surface layers is required. These data reduction techniques also provide a means of separating spectral features from layers that may have a moderate to high degree of spectral overlap or where contributions of individual components to spectral bands envelopes may not be known because spectra of the pure components may not be obtainable or known.

Figure 17:
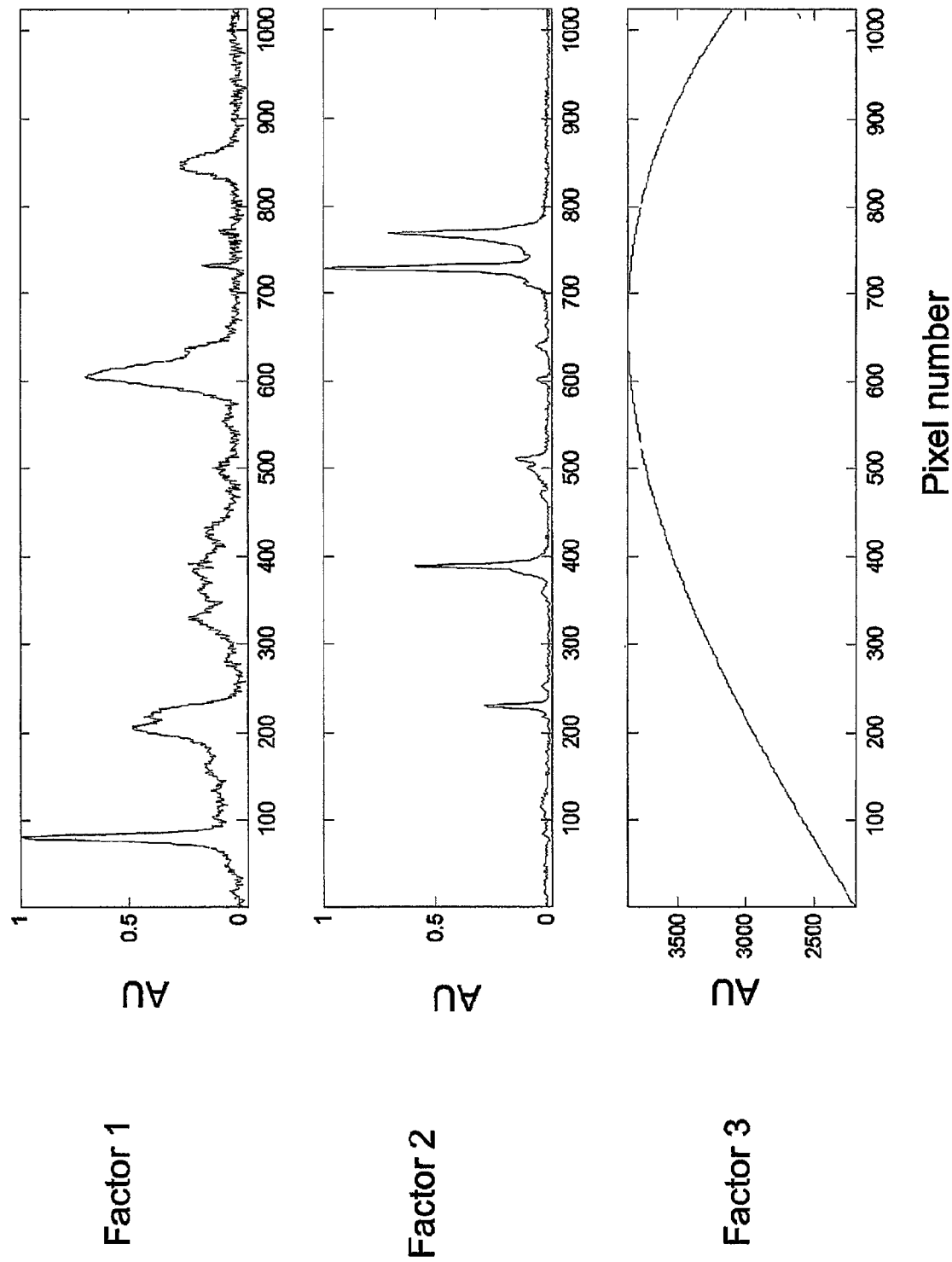
FIG. 17 shows the results of a PCA analysis of a series of Raman spectra for the same sample obtained using the analysis apparatus in accordance with the present invention.

The recovered factors from the multivariate analysis are shown in FIG. 17. The procedure cleanly decomposed the Raman spectra collected in this way into the pure spectra of the two individual layers, i.e. a PMMA (top layer) and a trans-stilbene (bottom layer). A factor for pure trans-stilbene was recovered by targeting the ca. 1595 cm$^{-1}$ band (pixel 730) and a factor for pure PMMA was recovered by targeting the ca. 809 cm$^{-1}$ band (pixel 80). The luminescence background factor was constructed from one of the original input spectra. This factor was generated using an iterative polynomial fitting algorithm (Lieber C A and Mahadevan-Jansen A 2003) typically used for baseline correction. In this case 100 fitting cycles using a third order polynomial were used to generate the baseline. This baseline was used as a factor representing the luminescence background. These three factors were then used to reconstruct the dataset with less than 3% error.

Although in the above example twenty separate Raman spectra were collected, where a scaled subtraction of individual Raman spectra is possible, as few as two or three spectra are required. Even with multivariate data analysis, although it is preferred to perform the analysis on at least a factor more than the number of components to be identified, such analysis can often be successfully performed using smaller data sets of, for example, around ten spectra.

The following is the inventors' current theory for explaining the efficacy of the analysis method and apparatus described herein. This theory is supported by Monte Carlo scattering modelling studies carried out by the inventors, which yield results in very good agreement with experiment. The variation in the relative content of Raman signals from different layers as the collection point is spatial offset originates from the random properties of the photon migration effect. The migrating photons in essence undergo a 'random walk' within the medium and the photon direction is randomised every transport length along the propagation distance. When a Raman signal is collected from the surface of a sample at the point where the probe beam is incident, the spectrum contains a relatively large signal contribution from the top layer due to the probe photon density being highest at the point of sample exposure. With increasing sample depth the probe intensity fast diminishes as the photon intensity is progressively diluted through the photon diffusion process. Moreover, Raman light generated at deeper layers of the sample is scattered as it propagates back to the surface and is subject to the same diffusion. This therefore leads to further dilution of the intensity of Raman spectra generated at deeper sample layers. This effect results in a substantially larger proportion of Raman photons generated at the sample surface being collected than those generated at deeper sample layers when a signal is collected from the surface of a sample at the point where the probe beam is incident, in comparison to the signal that would be collected for an optically transparent media probed in the same geometry.

However, when Raman light is collected from a point laterally offset from the point of probe beam incidence, the probe light intensity within the sample is becoming more equally distributed along its depth. This is because the incident light first had to propagate sideways through the sample from the probe incidence point to the collection area and was on its way randomised through photon diffusion. Consequently, the scattered Raman signal collected at a position offset from the probe incident point contains a higher proportion of the deeper layer signal than that in the spectrum collected from the probe beam incidence point.

The described spatial gating analysis apparatus and method thus offers an extremely powerful, yet simple means for extracting pure Raman signals from individual layers within diffusely scattering media. The probed sample depths can be well in excess of the transport length, which sets a depth limit on the conventional confocal Raman microscopy. In the above example, the transport length of the medium was estimated to be 200 µm. Importantly, the apparatus and method can be used 'blind', i.e. without any prior knowledge of the chemical constituents of individual layers. The technique has thus ideal prerequisites for sensitive sub-surface, non-destructive probing of diffusely scattering materials in both industrial and medical applications.

Figure 18:
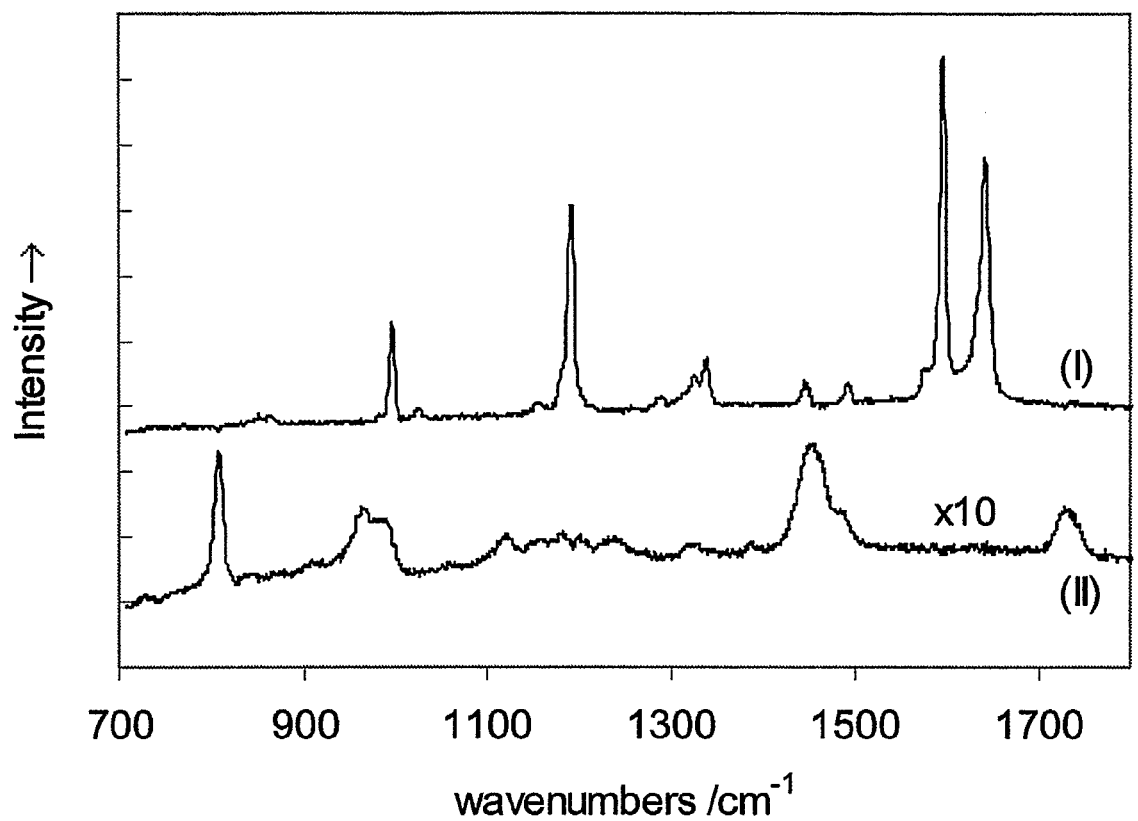
FIG. 18 shows the results of a simple subtraction process with respect to the same sample using Raman spectra obtained by the analysis method in accordance with the present invention.

In situations where a sample is known to consist of only two layers of different composition, such as in-vivo skin and bone layers, (if this is not known then this information can be obtained directly from pure PCA) the method and apparatus can be used to extract the pure signals of individual layers without the involvement of multivariate data analysis techniques. This is possible where the two spectra of the two layers each include an identifiable band or bands that do not overlap. In this situation a simple scaled subtraction can be used to separate the spectra of each of the individual layers from each other. In this process one Raman component is eliminated by a scaled subtraction of two spectra measured with two different spatial offsets cancelling out one or other spectral component in the process. The results of this simple extraction procedure are shown in FIG. 18. The spectra used in the analysis were measured with a zero and a 2 mm offset. The result is clearly satisfactory, although the applicability requires the above conditions to be satisfied. In contrast, the PCA analysis described above can be used in circumstances where there is no knowledge of the compositions of the different layers of a sample.

Thus, it will be apparent that it is not in all cases essential for a complete Raman spectrum to be generated with the present invention. Where there is some knowledge of the materials involved or the compositions to be detected, detection of individual Raman spectral features using, for example, one or more band pass filters is also encompassed by the SORS method and apparatus described herein.

The exact degree of the 'suppression' or separation of two layers in general situations depends on a variety of parameters. These parameters include the thickness of the top layer, that of the underlying matrix, the probe beam diameter, the exact collection geometry, the wavelength of the probe light used and the transport length of the medium. For non-invasive sub-surface probing, as a rule of thumb, it is believed that the ideal offset should be on the scale of the thickness or several thicknesses of the overlying medium. Also, for the technique to be effective the beam diameter should be smaller than the thickness of the top layer. In general terms the thinner the top layer is and the thicker the underlying matrix is favours a better spectral separation of the two components.

For this reason the present invention is particularly suited for use in non-invasive medical diagnosis applications. However, any degree of absorption of the probe or Raman photons will result in the overall yield of Raman signals from the sample surface being diminished. Therefore, for SORS analysis to be effective, it is important that the measurements be performed at wavelengths substantially free from any absorption. In the case of living tissue, this condition is well satisfied outside the haemoglobin absorption region (>600 nm) in the NIR (~800 nm). Thus, for living tissues the preferred laser source generates light at wavelengths of at least 600 nm. Laser sources generating light above 800 nm are also desirable as this reduces absorption of the incident light by melanin. Moreover, at this wavelength, bone tissue has relatively low fluorescence.

However, the use of light of wavelength 514 nm or >600 nm is not critical to this invention. The choice of probe wavelength is essentially a trade off between depth penetration, which improves with longer wavelength, and detector quantum efficiency, which is higher at shorter wavelengths. As mentioned earlier, the detector 103 used herein is a backilluminated deep depletion CCD detector based on silicon technology. This detector is selected as it the best sensitivity and signal-to-noise ratio of those that are currently available, but alternatives can be used. Longer wavelengths avoid exciting H2O modes in Raman spectra, but the cut-off limit for Si detection is 1.1 μm. InGaAs detectors can be used at longer wavelengths, but these have presently reduced sensitivity.

As an example of the potential medical applications of the SORS analysis, it is known that a Raman spectrum measured from bone tissue is indicative of its physio-chemical state. The peaks in the spectrum are indicative both of mineral components, such as phosphates, carbonates, hydroxides as well as interstitial and residual water molecules, and of organic material, primarily the collagen matrix. Relative intensities of mineral peaks and of collagen peaks should therefore be expected to differ from normal if there is an abnormality in bone structure.

The technology of generating chemically specific signatures buried within diffusely scattering matrices is applicable to many medical applications. In fact, it is envisaged that the non-destructive extraction of sub-surface information will have medical applications ranging across detection of embedded lesions and assessment of tumour, skin and blood compositions.

With the method and apparatus of the present invention, substantially pure Raman spectra can be retrieved from depths well in excess of those accessible with conventional confocal microscopy. Moreover, the present invention has the advantage that it is compatible with the use of cw lasers beams and is suited to remote monitoring in both industrial and medical applications.

The invention claimed is:

1. A method of determining, in vivo, one or more characteristics of a sub-surface tissue or fluid, through a diffusely scattering overlying tissue, comprising steps of:
    (a) supplying incident light as a continuous wave laser beam at one or more entry regions on a surface of the overlying tissue;
    (b) collecting, from one or more collection regions on the surface of the overlying tissue, light produced by scattering of said incident light within the overlying tissue, wherein the one or more collection regions on the surface are located at a plurality of spacings from the one or more entry regions on the surface;
    (c) detecting using a detector, in the collected light, a plurality of Raman features for said plurality of spacings, wherein one or more of the Raman features corresponds to each different spacing, said Raman features being spectrally related to the incident light and originating from the sub-surface tissue; and
    (d) determining said characteristics of the sub-surface tissue or fluid from said Raman features.

2. The method of claim 1, wherein the sub-surface tissue or fluid comprises one of bone, cartilage, breast tissue and blood.

3. The method of claim 1, wherein the overlying tissue comprises one of skin and nail.

4. The method of claim 1, wherein the step of detecting comprises spectrally dispersing the collected light to form a Raman spectrum.

5. The method of claim 1, wherein the step of detecting comprises filtering the collected light to isolate one or more of said Raman spectral features.

6. The method of claim 1, wherein determining said characteristic comprises associating the Raman features from different spacings with different depths or distributions of depth within the overlying tissue and sub-surface tissue or fluid.

7. The method of claim 1, wherein determining said characteristic comprises combining the Raman features from different spacings to select for a depth or distribution of depth.

8. The method of claim 1 wherein the step of collecting comprises collecting light from a plurality of collection regions spaced by different distances from a common entry region.

9. The method of claim 1 wherein one or more collection regions surround an entry region.

10. The method of claim 9, wherein each collection region is an annulus, and the scattered light is collected by a plurality of collection optical fibres distributed around one or more illumination optical fibres used to supply the incident radiation to the entry region.

11. The method of claim 1, wherein one or more entry regions surround a common collection region.

12. The method of claim 1 further comprising adjusting collection optics disposed in the path of the collected light to adjust the distance between a collection region and an entry region.

13. The method of claim 1 further comprising disposing one or more mirror elements adjacent to the surface of the overlying tissue, outside the collection region, to reflect light back into the tissue.

14. A method of determining whether a patient has a cancer condition in a target tissue, comprising:
carrying out the steps of claim 1 to measure, in the target tissue, one or more Raman spectral features characteristic of a cancer condition; and
determining, based on the Raman spectral features, whether the patient has a cancer condition in the target tissue.

15. A method of determining whether a patient has a medical condition related to bone tissues of the patient, comprising:
carrying out the steps of claim 1 to measure one or more Raman spectral features characteristic of the bone tissue; and
determining, based on the Raman spectral features, whether the patient has a bone tissue condition.

16. A method of diagnosis comprising collecting from a sample, consisting of a surface region of an overlying tissue and a sub-layer region of a deep tissue which is different to the overlying tissue, one or more Raman spectra using the method of claim 1.

17. A method of diagnosis as claimed in claim 16, further comprising identifying one or more features specific to the Raman spectrum of the sub-layer region of the sample in the one or more collected Raman spectra and comparing the one or more identified features with those obtained from a healthy control specimen.

18. The method of claim 1, wherein at one of the plurality of spacings the entry and collection regions are at the same place or substantially overlapping.

19. The method of claim 1, wherein the plurality of entry and collection regions are non-overlapping.

20. The method of claim 1, wherein said characteristics are determined from changes in intensities of the one or more Raman features between the different spacings.

21. A method of measuring, in-vivo, a sub-surface Raman spectrum of a diffusely-scattering tissue, comprising:
a) irradiating the tissue with a continuous wave laser beam light probe of incident radiation at a point of irradiation on the surface of the tissue;
b) collecting light scattered by the tissue; and
c) spectrally separating at least a portion of the collected light to detect one or more Raman spectral features, wherein light produced by scattering of said incident radiation by the tissue is collected from a plurality of spatial locations on the surface of the tissue, each spatial location being at a different distance from the point of irradiation, at least a portion of the light collected at each spatial location being separately spectrally dispersed to form a plurality of Raman spectra corresponding to said plurality of spatial locations such that a separate Raman spectrum corresponds to each spatial location; and
d) analysing the plurality of Raman spectra to extract information on the Raman spectrum of a sub-surface region of the tissue.

22. A method as claimed in claim 21, wherein at least two Raman spectra are collected and are analysed using a scaled subtraction, the Raman spectrum collected at a distance closest to the point of irradiation being subtracted from the Raman spectrum collected further from the point of irradiation, whereby features of the Raman spectrum for a sub-layer of the tissue are identified.

23. A method as claimed in claim 21, wherein the Raman spectrum for the chemical composition of the surface of the tissue is known and the Raman spectra are analysed by scaled subtraction of the known Raman spectrum from the Raman spectra of the collected light.

24. A method as claimed in claim 21, wherein the plurality of Raman spectra are analysed using multivariate data analysis.

25. A method as claimed in claim 24, wherein the plurality of Raman spectra are analysed using principal component analysis.

26. A method as claimed in claim 24, wherein at least twenty Raman spectra are collected at different distances from the point of irradiation.

27. A method as claimed in claim 21, wherein the tissue is irradiated at two or more different wavelengths and the collected light is a combination of a Raman spectrum and fluorescence and wherein the method comprises the further step of extracting the Raman spectrum from the collected light.

28. A method as claimed in claim 21, wherein at least one of the tissue, the collection optics and the point or region of irradiation is moved relative to the others to enable the collection of Raman spectra at different distances from the point of irradiation.

29. A method as claimed in claim 28, wherein a movable stage is provided on which the tissue is mounted and the probe beam is arranged to track the movement of the tissue whereby the tissue is moved relative to fixed collection optics for the collection of scattered light at different distances from the point of irradiation.

30. A method as claimed in claim 29, wherein the scattered light is collected from point regions at different distances from the point of irradiation.

31. A method as claimed in claim 29, wherein the scattered light is collected from a plurality of substantially parallel lines substantially transverse to the distance as measured from the point of irradiation.

32. A method as claimed in claim 18, wherein the light probe comprises two or more separate wavelengths and is generated by one or more lasers.

33. A method as claimed in claim 32, wherein the light probe is generated by a single tunable laser.

34. A method as claimed in claim 32, wherein the two or more separate wavelengths of the light probe are generated by two or more respective lasers.

35. A method as claimed in claim 21, wherein the probe beam is supplied using optical fibres and the scattered light is collected using optical fibres arranged in a plurality of concentric circles around the probe beam optical fibres whereby the scattered light is collected in concentric rings at differing radii from the point of irradiation.

36. A method as claimed in claim 21, wherein the collected light is spectrally dispersed using a spectrometer in combination with a CCD camera.

37. The method of claim 21, wherein the incident radiation has a wavelength greater than 600 nm.

38. The method of claim 21, wherein the incident radiation has a wavelength greater than 800 nm.

39. A method of carrying out an in-vivo sub-cutaneous inspection of a sub-surface tissue or fluid without surgical intervention, comprising:
    irradiating a surface tissue with a continuous wave laser beam;
    collecting light scattered beneath the surface, from one or more collection regions on the surface, said one or more collection regions being located at a plurality of spacings from an incidence location of the laser beam on the surface tissue; and
    detecting, using a detector, one or more Raman spectral features from the collected light for each spacing,
    wherein the sub-surface tissue or fluid is one of bone, cartilage and blood.

40. The method of claim 39, wherein the collection regions do not overlap the laser beam.

41. Apparatus for determining, in-vivo, one or more characteristics of a sub-surface tissue or fluid, through a diffusively scattering overlying tissue, comprising:
    a light source arranged to supply incident light as a continuous wave laser beam at one or more entry regions on a surface of the overlying tissue;
    a collector arranged to collect light scattered within the overlying tissue, from one or more collection regions on the surface of the overlying tissue, wherein the one or more collection regions on the surface are located at a plurality of spacings from the one or more entry regions on the surface;
    a detector arranged to detect, in the collected light, a plurality of Raman features for said plurality of spacings, wherein at least one Raman feature corresponds to each spacing, said Raman features being spectrally related to the incident light, which originate from the sub-surface tissue or fluid; and
    an analyzer adapted to derive, from the Raman features, one or more characteristics of the sub-surface tissue or fluid.

42. The apparatus of claim 41, adapted to collect light from multiple spacings between the entry and collection region, said analyzer being adapted to combine the Raman features from said multiple spacings to select for a depth or distribution of depth.

43. The apparatus of claim 41, wherein the sub-surface tissue comprises at least one of bone, cartilage, breast tissue and blood.

44. The apparatus of claim 41, wherein the overlying tissue comprises at least one of skin and nail.

45. The apparatus of claim 41, wherein the detector comprises a spectrometer arranged to spectrally disperse the collected light to separate out said Raman features.

46. The apparatus of claim 41, wherein the detector comprises one or more filters arranged to select said Raman features.

47. The apparatus of claim 41, wherein either the entry region or the collection region is an annular region surrounding the other of the two regions.

48. The apparatus of claim 47 further comprising an optics arrangement adapted to controllably adjust the diameter of the annular region.

49. The apparatus of claim 41, further comprising a masking device arranged to controllably adjust the spacing between the entry region and the collection region.

50. The apparatus of claim 41 further comprising one or more mirror elements disposed adjacent to the overlying tissue surface outside the one or more collection and entry regions, so as to reflect light back into the tissue.

51. The apparatus of claim 41, wherein the incident radiation has a wavelength greater than 600 nm.

52. The apparatus of claim 41, wherein the incident radiation has a wavelength greater than 800 nm.

53. The apparatus of claim 41 implemented as an endoscope for inspection within the body by access through a natural or surgically formed orifice.

54. The apparatus of claim 41, wherein at one of the plurality of spacings the entry and collection regions are at the same place or substantially overlapping.

55. The apparatus of claim 41, wherein the plurality of entry and collection regions are non-overlapping.

56. The apparatus of claim 41, wherein the analyzer is adapted to derive the characteristics from changes in intensities of the one or more Raman features between the different spacings.

57. Apparatus for in-vivo selective measurement of Raman spectra generated at different depths within a diffusely-scattering tissue, the apparatus comprising:
    a light source for irradiating the tissue with a continuous wave laser probe beam of incident radiation;
    collection optics for collecting light scattered by the tissue and passing it to a spectrometer;
    detection means for detecting light dispersed by the spectrometer,
    wherein the apparatus is adapted for scattered light to be collected at a plurality of spatial locations on the surface of the tissue, each spatial location being at a different distance from a point of irradiation on the tissue and at least a portion of the light collected at each spatial location being separately spectrally dispersed by the spectrometer to form a plurality of Raman spectra corresponding to said plurality of spatial locations, and wherein the apparatus further includes an analyser for identifying features specific to the Raman spectrum of a sub-layer of the tissue from the plurality of Raman spectra.

58. Apparatus as claimed in claim 57, wherein the analyser is adapted to perform a scaled subtraction between Raman spectra.

59. Apparatus as claimed in claim 57, wherein the analyser is adapted to perform multivariate data analysis on the Raman spectra.

60. Apparatus as claimed in claim 59, wherein the analyser is adapted to perform principal component analysis on the Raman spectra.

61. Apparatus as claimed in claim 57, further comprising a movable stage for relative movement of at least one of the tissue, the collection optics and the point of irradiation to enable the collection of Raman spectra at different distances from the point of irradiation.

62. Apparatus as claimed in claim 61, wherein the movable stage is a movable sample stage and wherein means are provided for tracking the probe beam with respect to movement of the tissue whereby the sample may be moved relative to the fixed collection optics to enable scattered light to be collected at a plurality of distances from the point of irradiation.

63. Apparatus as claimed in claim 57, wherein the collection optics comprises optical fibres arranged in a plurality of concentric circles around the probe beam.

64. Apparatus as claimed in claim 57, wherein the detection means comprises a CCD camera.

65. Medical sub-cutaneous inspection apparatus for carrying out an in-vivo inspection of a sub-surface tissue without surgical intervention, comprising:
- a probe light beam source arranged to irradiate a surface tissue with a continuous wave laser beam;
- a collector arranged to collect light scattered beneath the surface, from one or more collection regions on the surface, said one or more collection regions being located at a plurality of spacings from an incidence location of the laser beam on the surface tissue;
- a detector arranged to detect one or more Raman spectral features from the collected light for each spacing; and
- an analyzer arranged to derive one or more characteristics of the sub-surface tissue from intensities of the Raman spectral features.

66. The apparatus of claim 65, wherein the collection regions do not overlap with the laser beam.

* * * * *